United States Patent
Candi et al.

(10) Patent No.: US 9,096,852 B2
(45) Date of Patent: Aug. 4, 2015

(54) INHIBITORS OF MICRO-RNAS FOR USE FOR PREVENTING AND/OR ATTENUATING SKIN AGEING AND/OR FOR HYDRATING SKIN

(75) Inventors: Eleonora Candi, Rome (IT); Gennaro Melino, Rome (IT); Gaelle Saintigny, Paris (FR); Christian Mahe, Neuilly sur Seine (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 30 days.

(21) Appl. No.: 13/700,839

(22) PCT Filed: Jun. 7, 2011

(86) PCT No.: PCT/EP2011/059392
§ 371 (c)(1),
(2), (4) Date: Nov. 29, 2012

(87) PCT Pub. No.: WO2011/154402
PCT Pub. Date: Dec. 15, 2011

(65) Prior Publication Data
US 2013/0071370 A1 Mar. 21, 2013

Related U.S. Application Data

(63) Continuation of application No. 12/797,270, filed on Jun. 9, 2010, now abandoned.

(30) Foreign Application Priority Data

Jun. 9, 2010 (EP) ..................... 10305617

(51) Int. Cl.
C12N 15/113 (2010.01)
C12Q 1/68 (2006.01)
G01N 33/50 (2006.01)

(52) U.S. Cl.
CPC ............ *C12N 15/113* (2013.01); *C12Q 1/6883* (2013.01); *G01N 33/5044* (2013.01); *C12N 2310/141* (2013.01); *C12N 2320/11* (2013.01); *C12Q 2600/148* (2013.01); *C12Q 2600/178* (2013.01)

(58) Field of Classification Search
USPC ......... 435/6, 91.1, 455, 6.1, 91.31, 377, 6.12, 435/6.13, 325; 514/1, 2, 44, 44 A, 44 R; 424/9.1, 9.2, 93.21; 536/23.1, 24.5, 536/24.31
See application file for complete search history.

(56) References Cited

U.S. PATENT DOCUMENTS

| | | |
|---|---|---|
| 2004/0185561 A1* | 9/2004 | Cook ............................ 435/405 |
| 2007/0281314 A1* | 12/2007 | Benson ............................ 435/6 |
| 2008/0009508 A1 | 1/2008 | Szucova et al. |
| 2010/0202973 A1* | 8/2010 | Pivarcsi et al. ................. 424/9.2 |
| 2011/0190372 A1* | 8/2011 | Tomic-Canic et al. ...... 514/44 A |
| 2012/0035068 A1* | 2/2012 | Ferguson et al. .................. 506/9 |
| 2012/0207744 A1* | 8/2012 | Mendlein et al. .......... 424/130.1 |
| 2013/0143945 A1* | 6/2013 | Brown et al. ............... 514/44 A |
| 2014/0031415 A1* | 1/2014 | Brown et al. ............... 514/44 A |
| 2014/0272998 A1* | 9/2014 | Ralfkiaer et al. ............ 435/6.12 |

FOREIGN PATENT DOCUMENTS

WO 2009/066967 A2 5/2009

OTHER PUBLICATIONS

Lu et al. MicroRNA expression profiles classify human cancers. Nature. 2005;435:834-838.*
Sommer et al., Cell Cycle, vol. 5, No. 17, pp. 2005-2011 (2006).*
Yi et al., Nature, vol. 452, pp. 225-230 (2008).*
Lena et al., Cell Death and Differentiation, vol. 15, pp. 1187-1195 (2008).*
Yi et al., Nature, vol. 452, pp. 225-229 (2008).*
Aberdam et al., Trends in Biochem. Sci., vol. 33, No. 12, pp. 583-591 (2008).*
Lena A M et al.: "miR-203 represses 'sternness' by repressing DeltaNp63.", Cell Death and Differentiation Jul. 2008, LNKD-Pubmed:18483491, vol. 15, No. 7, Jul. 2008 , pp. 1187-1195, XP002614115, ISSN: 1350-9047, abstract 1-10,12 p. 1192; figure 4.
International Search Report, dated Sep. 27, 2011, from corresponding PCT application.

* cited by examiner

*Primary Examiner* — Jane Zara
(74) *Attorney, Agent, or Firm* — Young & Thompson

(57) ABSTRACT

Method of identifying and using compounds which inhibit the expression or activity of micro-RNAs for preventing and/or attenuating ageing, and/or for hydrating skin. An in vitro method for screening for candidate compounds for preventing and/or attenuating ageing of the skin, and/or for hydrating the skin, includes the following steps:
  a. bringing at least one test compound in contact with a sample of keratinocytes;
  b. measuring the expression or the activity of at least one microRNA in the keratinocytes;
  c. selecting the compounds for which an inhibition of at least 20%, preferably at least 30%, preferably at least 40% of the expression or an inhibition of at least 20%, preferably at least 30%, preferably at least 40% of the activity of at least one microRNA is measured in the keratinocytes treated in a. compared with the untreated keratinocytes.

6 Claims, 14 Drawing Sheets

SEQUENCE LISTING

```
<160> NUMBER OF SEQ ID NOS: 16

<210> SEQ ID NO 1
<211> LENGTH: 89
<212> TYPE: RNA
<213> ORGANISM: Artificial
<220> FEATURE:
<223> OTHER INFORMATION: MicroRNA

<400> SEQUENCE: 1
ugcugcuggc cagagcucuu uucacauugu gcuacugucu gcaccuguca cuagcagugc    60
aauguuaaaa gggcauuggc cguguagug                                     89

<210> SEQ ID NO 2
<211> LENGTH: 99
<212> TYPE: RNA
<213> ORGANISM: Artificial
<220> FEATURE:
<223> OTHER INFORMATION: MicroRNA
```

```
<400> SEQUENCE: 2
cccuggcaug gugugguggg gcagcuggug uugugaauca ggccguugcc aaucagagaa    60
cggcuacuuc acaacaccag ggccacacca cacuacagg                           99

<210> SEQ ID NO 3
<211> LENGTH: 110
<212> TYPE: RNA
<213> ORGANISM: Artificial
<220> FEATURE:
<223> OTHER INFORMATION: MicroRNA

<400> SEQUENCE: 3
ugaguuuuga gguugcuuca gugaacauuc aacgcugucg gugaguuugg aauuaaaauc    60
aaaaccaucg accguugauu guacccuaug gcuaaccauc aucuacucca              110

<210> SEQ ID NO 4
<211> LENGTH: 92
<212> TYPE: RNA
<213> ORGANISM: Artificial
<220> FEATURE:
<223> OTHER INFORMATION: MicroRNA

<400> SEQUENCE: 4
cggcuggaca gcgggcaacg gaaucccaaa agcagcuguu gucuccagag cauuccagcu    60
gcgcuuggau uucguccccu gcucuccugc cu                                  92

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
ggccactagt gcctcaccat gtgagctctt c                                   31

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
ggccactagt gcatgtcctg gcaaacaaaa agag                                34

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
ttaaatgaaa gaaaattgag tattgaccat tttttaatt                           39

<210> SEQ ID NO 8
<211> LENGTH: 39
<212> TYPE: DNA
<213> ORGANISM: Artificial Sequence
<220> FEATURE:
<223> OTHER INFORMATION: primer
```

<400> SEQUENCE: 8
aattaaaaaa tggtcaatac tcaattttct ttcatttaa         39

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gaccctagga gatgatcaag aggc         24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gcctaggaag ctgtacaaat tgct         24

<210> SEQ ID NO 11
<211> LENGTH: 39
<212> TYPE: DNA
<213> ORGANISM: Artificial Sequence
<220> FEATURE:
<223> OTHER INFORMATION: primer

<400> SEQUENCE: 11
gcaggtacag gaattgttcc ttaggaactt tagcatgtc         39

<210> SEQ ID NO 12
<211> LENGTH: 39
<212> TYPE: DNA
<213> ORGANISM: Artificial Sequence
<220> FEATURE:
<223> OTHER INFORMATION: primer

<400> SEQUENCE: 12
gacatgctaa agttcctaag gaacaattcc tgtacctgc         39

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gaccctagga gatgatcaag aggc         24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
gcctaggaag ctgtacaaat tgct         24

```
<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
ggaactttag catgtcaaaa ttacttgtga actcgataga                    40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
tctatcgagt tcacaagtaa ttttgacatg ctaaagttcc                    40
```

INHIBITORS OF MICRO-RNAS FOR USE FOR PREVENTING AND/OR ATTENUATING SKIN AGEING AND/OR FOR HYDRATING SKIN

FIELD OF THE INVENTION

The invention relates to the identification and the use of compounds which inhibit the expression or activity of micro-RNAs for preventing and/or attenuating ageing, and/or for hydrating skin.

BACKGROUND OF THE INVENTION

Cellular senescence is a form of irreversible growth arrest, originally described for end-stage proliferative cells in culture, but known to be induced by several stimuli such as DNA damage, oxidative stress, chemotherapy and excess of mitotic stimuli such as oncogenic activation (Serrano et al 1997; Campisi 2001; Schmitt et al 2002). Cells enter in a stage of irreversible arrest, showing distinctive features, including enhanced beta-galactosidase activity and increased expression of key mediators including p53, promyelocitic leukemia protein (PML), p16INK4a and p19Arf (Serrano et al 1997; Narita et al 2003; Sharpless et al 2004). Although mostly studied in vitro, cellular senescence has been correlatively linked to the aging process at the level of the whole animal, thus implicating many of the factors that regulate senescence as contributing to organism aging (Sharpless and DePinho 2004, Campisi 2005).

Recent findings identify the p53-related protein p63, as a key molecule linking senescence and aging (Keyers et al 2005; Sommer et al 2006). Indeed, p63 heterozygous mice have a shortened life span and display features of accelerated aging. Both germline and somatic p63 deficient cells present enhanced expression of beta-galactosidase activity, PML and p16INK4a, demonstrating that p63 deficiency accelerated the aging phenotype (Keyers et al 2005). Beside the involvement in aging, the transcription factor p63 has an important role in development due to its ability to regulate epithelial proliferation, differentiation and cell fate. p63 KO mice exhibit several epithelial defects, including absence of skin, hair and ectodermal derivatives (Yang et al 1999; Mills et al 1999). Some reports indicate that p63 is essential for maintaining the stem cell pool of the epidermis (Seeno et al 2007). Recently, it has been reported that p63 is also regulated by microRNAs. In particular, it has been shown that miR-203, by targeting p63, controls the proliferative potential of basal layer keratinocytes (Lena et al 2008; Yi et al 2008), thus controlling the crucial transition among basal and spinous layer.

SirT-1 (or Sirt-1) is also a key molecule linking senescence and aging. It's a $NAD^+$-dependent deacetylase that regulates gene expression by deacetylation of lysine residues on histones, transcription factor and co-factors. Cells with SirT-1 gain of function improves metabolic efficiency, promoting longevity and resistance to diseases (Haigis M C, Guarente L P. Mammalian sirtuins-emerging roles in physiology, aging, and calorie restriction. Genes Dev. 2006. 1; 20(21):2913-21). In addition it as been known that SirT-1 has a protective effects against endothelial dysfunction by preventing stress-induced senescence (Potente M, Ghaeni L, Baldessari D, Mostoslaysky R, Rossig L, Dequiedt F, Haendeler J, Mione M, Dejana E, Alt F W, Zeiher A M, Dimmeler S. SIRT1 controls endothelial angiogenic functions during vascular growth. Genes Dev. 2007. 21(20):2644-58). Recently, it has been shown that SirT-1 is regulated by the microRNA miR-217 in endothelial cell senescent system (Menghini R, Casagrande V, Cardellini M, Martelli E, Terrinoni A, Amati F, Vasa-Nicotera M, Ippoliti A, Novelli G, Melino G, Lauro R, Federici M. MicroRNA 217 modulates endothelial cell senescence via silent information regulator 1. Circulation. 2009. 120(15):1524-32).

CDK6 was identified as a new member in a family of vertebrate cdc-2 related kinases. This novel kinase was found to partner with the D-type cyclins and to possess pRb kinase activity in vitro and has since been understood to function solely as a pRb (retinoblastoma) kinase in the regulation of the G(1) phase of the cell cycle. In the past 2 years, several independent studies in multiple cell types have indicated a novel role for cdk6 in differentiation. The mechanism of cdk6 function in differentiation is not understood, but it may extend beyond the established role of cdk6 as a pRb kinase. As this story unfolds it will be important to discover if the function of cdk6 in differentiation is pRb-dependent or pRb-independent, since pRb has long been established as a key factor in initiating and maintaining cell cycle exit during differentiation (Kohrt D M et al., Cycle. 2009 1; 8(17):2837-43; Grossel M J, et al., J Cell Biochem. 2006; 97(3):485-93). Cdk-6 has never been described before to be involved in senescence.

MicroRNAs (miRs) are single-stranded RNA molecules that regulate the expression of messenger mRNA. miRs are generated as pre-microRNA transcripts that are imported into the cytoplasm, where they are cleaved by Dicer, a ribonuclease III-like enzyme. In mammals Dicer plays important roles in cell differentiation and tissue morphogenesis and ablation of Dicer in mice induces embryonic lethality at developmental stage E6-E7 (Bernstein et al 2003). Ablation of Dicer in embryonic fibroblasts induces a premature senescence phenotype that was also observed in vivo after Dicer ablation in the developing limb and adult skin (Mudhasani et al 2008). The mature miRs negatively regulate gene expression by targeting specific messenger mRNAs for cleavage or translation repression. Growing body of evidence suggests that they are involved in the control of a wide range of physiological pathways including cellular senescence.

It is thus desirable and important to provide products or active agents which prevent, reduce or even inhibit the cellular senescence, particularly the keratinocyte senescence.

The present invention thus provides a method for identifying such useful agents.

SUMMARY OF THE INVENTION

The present invention thus relates to an in vitro method for screening for candidate compounds for preventing and/or attenuating ageing of the skin, and/or for hydrating the skin, comprising the following steps:
  a. bringing at least one test compound into contact with a sample of keratinocytes;
  b. measuring the expression or the activity of at least one microRNA in said keratinocytes;
  c. selecting the compounds for which an inhibition of at least 20%, preferably at least 30%, preferably at least 40% of the expression or an inhibition of at least 20%, preferably at least 30%, preferably at least 40% of the activity of at least one microRNA is measured in the keratinocytes treated in a. compared with the untreated keratinocytes.

Preferably, the keratinocytes are pre-senescent keratinocytes. Thus, the present invention relates to an in vitro method for screening for candidate compounds for preventing and/or attenuating ageing of the skin, and/or for hydrating the skin, comprising the following steps:

a. bringing at least one test compound into contact with a sample of pre-senescent keratinocytes;

b. measuring the expression or the activity of at least one microRNA in said pre-senescent keratinocytes;

c. selecting the compounds for which an inhibition of at least 20%, preferably at least 30%, preferably at least 40% of the expression or an inhibition of at least 20%, preferably at least 30%, preferably at least 40% of the activity of at least one microRNA is measured in the pre-senescent keratinocytes treated in a. compared with the untreated pre-senescent keratinocytes.

By "pre-senescent keratinocytes", it is meant cells which express p16 at a detectable level (this level can be determined by Western blot), but which do not express beta-galactosidase; they are beta-gal negative. These cells proliferate slower than young keratinocytes.

According to a first embodiment, step b. is performed before and after step a. In this case, the expression or activity of the microRNA measured in the keratinocytes, preferably pre-senescent, before step a. corresponds to the control value (i.e. untreated keratinocytes, preferably pre-senescent). Thus, step c. comprises the selection of the compounds for which an inhibition of at least 20%, preferably at least 30%, preferably at least 40% of the expression or an inhibition of at least 20%, preferably at least 30%, preferably at least 40% of the activity of at least one microRNA is measured in the keratinocytes, preferably pre-senescent, treated in a. compared with the same keratinocytes, preferably pre-senescent, before step a.

According to another embodiment, the method comprises a first step a'. of preparing samples of keratinocytes, preferably pre-senescent. Thus, preferably, the present invention relates to an in vitro method for screening for candidate compounds for preventing and/or attenuating ageing of the skin, and/or for hydrating the skin, comprising the following steps:

a'. preparing at least two samples of keratinocytes, preferably pre-senescent;

a. bringing one of the samples into contact with at least one test compound; then b. measuring the expression or the activity of at least one microRNA in said samples; and c. selecting the compounds for which an inhibition of at least 20%, preferably at least 30%, preferably at least 40% of the expression or an inhibition of at least 20%, preferably at least 30%, preferably at least 40% of the activity of at least one microRNA is measured in the keratinocytes, preferably pre-senescent, treated in a. compared with the sample of untreated keratinocytes, preferably pre-senescent.

In this second embodiment, the expression or activity of the microRNA measured in the sample of keratinocytes, preferably pre-senescent, not submitted to step a. corresponds to the control value (i.e. untreated keratinocytes, preferably pre-senescent).

DETAILED DESCRIPTION OF THE INVENTION

By the expression "ageing of the skin" is intended any change in the external appearance of the skin due to ageing, whether this is chronobiological and/or photo-induced, such as, for example, wrinkles and fine lines, withered skin, flaccid skin, thinned skin, and skin lacking elasticity and/or tonus, and also any internal change in the skin which is not systematically reflected by a changed external appearance, such as, for example, any internal degradation of the skin, particularly of collagen, following exposure to ultraviolet radiation.

By "hydrating the skin", it is meant maintaining the natural humidity of the skin and preventing its drying.

Preferably, the miRs of interest in step b. target the p63 protein and/or the p63 mRNA and/or the corresponding gene (i.e. TP63 in humans). Thus preferably, the miRs of interest in step b. target the TP63 gene or the p63 mRNA.

Preferably, miRs are chosen from the group consisting of miR-130a, miR-138, miR-181a and miR-191.

miR-130a is of SEQ ID No. 1. It is the sequence HGNC: 31514;

miR-138 is of SEQ ID No. 2. It is the sequence HGNC: 31524;

miR-181a is of SEQ ID No. 3. It is the sequence HGNC: 31590;

miR-191 is of SEQ ID No. 4. It is the sequence HGNC: 31561.

These sequences come from the HGNC database.

The test compounds tested may be of any type. They may be of natural origin or may have been produced by chemical synthesis. This may involve a library of structurally defined chemical compounds, uncharacterized compounds or substances, or a mixture of compounds.

Natural compounds include compounds from animal or vegetal origin, like plants and animals. Preferably, the test compounds are vegetal, preferably chosen from botanical extracts.

The pre-senescent keratinocytes used in steps a'. and a. above are a cellular model for replicative senescence. These pre-senescent keratinocytes are obtained after 37 population doublings in classical culture conditions. The classical culture conditions comprise a culture of the keratinocytes in Epilife medium added with HKGS growth supplements, constantly kept in a subconfluent state.

Preferably, they are obtained thanks to the following process:

Human Primary Epidermal Keratinocytes, neonatal are cultured in an appropriate medium. Such a medium may be EpiLife medium added with HKGS growth supplements. They are constantly kept subconfluent. Cells are passaged at appropriate periods of time, usually once a week.

At each passage, a portion of the cells is collected and analyzed to measure population doublings, population doubling time, senescence biochemical markers and cell cycle.

The population doublings of primary human keratinocytes is measured during 40 days of culture. After 37 population doublings the growth curve has a plateau, showing that cells stop dividing and are reaching the senescent state. Analysis of proliferation marker (p63), differentiation marker (K10) and senescent markers (p16/INK) suggest that while the proliferation marker decreases, the cells are not differentiating. Cells undergo replicative senescence after the fourth passage at 37 population doublings. In addition, the percentage of proliferating cells is diminishing during senescence.

According to step a., the test compound is put into contact with a sample of keratinocytes, preferably pre-senescent.

According to step b., the expression and/or the activity of at least one microRNA is measured in said keratinocytes, preferably pre-senescent.

The term "expression of a microRNA" is intended to mean the amount of produced microRNA.

The term "activity of a microRNA" is intended to mean the ability of said microRNA to inhibit the level of the mRNA to which it hybridizes.

Those skilled in the art are familiar with the techniques for quantitatively or semi-quantitatively detecting the mRNA to which said microRNA hybridizes, and thus, determining said microRNA activity. Techniques based on hybridization of the mRNA with specific nucleotide probes are the most common, like Northern blotting, RT-PCR (reverse transcriptase polymerase chain reaction), quantitative RT-PCR (qRT-PCR).

Those skilled in the art are also familiar with the techniques for quantitatively or semi-quantitatively detecting the microRNA, or the mRNA to which said microRNA hybridizes. In particular, the expression of the microRNA can be measured by real-time PCR. The activity of the microRNA can be measured by real-time PCR on the mRNA targets, or by evaluating the protein level of the target by Western blot. Alternatively, if the target is unknown, the activity of the microRNA can be tested by evaluating the biological effect of the microRNA itself, such as an effect on beta-gal staining or on proliferation.

Preferably, the expression of the microRNA is measured by real-time PCR.

The expression or activity of the microRNA after treatment with the test compound is then compared to a control value, i.e. a value obtained in the same keratinocytes (preferably pre-senescent) before treatment, or a value obtained in another sample of keratinocytes (preferably pre-senescent) which are untreated.

According to step c., the useful compounds are those for which an inhibition of at least 20%, preferably at least 30%, preferably at least 40% of the expression or an inhibition of at least 20%, preferably at least 30%, preferably at least 40% of the activity of at least one microRNA is measured in the treated keratinocytes, preferably pre-senescent, compared with untreated keratinocytes, preferably pre-senescent. Preferably, the inhibition of the expression or of the activity of said microRNA is of at least 50%, preferably of at least 60%.

The compounds selected by means of the screening methods defined herein can subsequently be tested on other in vitro models and/or in vivo models (in animals or humans) for their effects on skin ageing and/or skin hydration. The useful compounds according to the invention are inhibitors of the targeted microRNA.

A subject of the invention is also the cosmetic use of an inhibitor of at least one microRNA, said inhibitor being identified according to the above described method, for preventing and/or attenuating ageing of the skin and/or for hydrating the skin.

According to another aspect, an objet of the present invention is the use of at least one microRNA inhibitor, said inhibitor being identified according to the above described method, to make a therapeutic composition for preventing and/or attenuating ageing of the skin and/or for hydrating the skin. The present invention thus also relates to the use of at least one microRNA inhibitor, said inhibitor being identified according to the above described method, for preventing and/or attenuating ageing of the skin and/or for hydrating the skin.

The inhibitor refers to a compound which eliminates or substantially reduces the expression or activity of the microRNA. The term "substantially" signifies a reduction of at least 20%, preferably at least 30%, preferably at least 40%, preferably of at least 50%, and more preferably of at least 60%.

The microRNA inhibitor can be used in a proportion of from 0.001 to 10% by weight, preferably in a proportion of from 0.01 to 5% by weight of the composition.

The inhibitor may be an antisense DNA or RNA polynucleotide or a siRNA. Preferably, inhibitors of microRNA (miR) are anti-miRs.

Anti-miRs are miR inhibitors that specifically inhibit endogenous miRs. Anti-miRs are single stranded nucleic acids designed to specifically bind to and inhibit endogenous microRNA molecules. Anti-miRs have nucleic sequence complementary to the sequence of the target miR. These ready-to-use inhibitors can be introduced into cells using transfection or electroporation parameters similar to those used for siRNAs, and enable detailed study of miR biological effects. Use of the anti-miR enables miR functional analysis by down-regulation of miR activity.

Anti-miRs are commercially available; they can for example be obtained by Ambion or Applied Biosystems.

Based on literature, it is possible that 70% inhibition of miR expression will have an effect on induction/inhibition of senescence in human normal cells (Menghini R, Casagrande V, Cardellini M, Martelli E, Terrinoni A, Amati F, Vasa-Nicotera M, Ippoliti A, Novelli G, Melino G, Lauro R, Federici M., MicroRNA 217 modulates endothelial cell senescence via silent information regulator 1. Circulation. 2009; 120(15):1524-32).

The miR inhibitors identified thanks to the screening method described above can be formulated within a composition, in combination with a physiologically acceptable carrier, preferably a cosmetically acceptable medium, i.e. a medium that is suitable for use in contact with human skin without any risk of toxicity, incompatibility, instability or allergic response and especially that does not cause any sensations of discomfort (redness, tautness, stinging, etc.) that are unacceptable to the user. These compositions may be administered, for example, orally, or topically. Preferably, the composition is applied topically. By oral administration, the composition may be in the form of tablets, gel capsules, sugar-coated tablets, syrups, suspensions, solutions, powders, granules, emulsions, suspensions of microspheres or nanospheres or lipid or polymeric vesicles for controlled release. By topical administration, the composition is more particularly for use in treating the skin and the mucous membranes and may be in the form of salves, creams, milks, ointments, powders, impregnated pads, solutions, gels, sprays, lotions or suspensions. It may also be in the form of suspensions of microspheres or nanospheres or lipid or polymeric vesicles or polymeric patches or hydrogels for controlled release. This composition for topical application may be in anhydrous form, in aqueous form or in the form of an emulsion. The composition for topical application may be in the form of an oil-in-water, water-in-oil or multiple emulsion (W/O/W or O/W/O), which may optionally be microemulsions or nano-emulsions, or in the form of an aqueous dispersion, a solution, an aqueous gel or a powder. In a preferred variant, the composition is in the form of a gel, a cream or a lotion.

The physiologically acceptable carrier of the composition generally comprises water and optionally other solvents such as ethanol.

This composition is preferably used as a care and/or cleansing product for facial and/or bodily skin and it may especially be in the form of a fluid, a gel or a mousse, conditioned, for example, in a pump-dispenser bottle, an aerosol or a tube, or in the form of cream conditioned, for example, in a jar. As a variant, it may be in the form of a makeup product and in particular a foundation or a loose or compact powder.

It may comprise various adjuvants, such as at least one compound chosen from:
  oils, which may be chosen especially from: linear or cyclic, volatile or non-volatile silicone oils, such as polydimethylsiloxanes (dimethicones), polyalkylcyclosiloxanes (cyclomethicones) and polyalkylphenylsiloxanes (phenyl dimethicones); synthetic oils such as fluoro oils, alkylbenzoates and branched hydrocarbons such as polyisobutylene; plant oils and especially soybean oil or jojoba oil; and mineral oils such as liquid petroleum jelly;

waxes such as ozokerite, polyethylene wax, beeswax or carnauba wax;

silicone elastomers obtained especially by reaction, in the presence of a catalyst, of a polysiloxane containing at least one reactive group (especially hydrogen or vinyl) and bearing at least one alkyl group (especially methyl) or phenyl, in a terminal and/or side position, with an organosilicone such as an organohydrogenopolysiloxane;

surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alkyl ethers of polyethylene glycol; alkylpolyglucosides; polysiloxane-modified polyethers; betaine and derivatives thereof; polyquaterniums; ethoxylated fatty alkyl sulfate salts; sulfosuccinates; sarcosinates; alkyl and dialkyl phosphates, and salts thereof; and fatty acid soaps;

co-surfactants such as linear fatty alcohols and in particular cetyl alcohol and stearyl alcohol;

thickeners and/or gelling agents, and in particular crosslinked or non-crosslinked, hydrophilic or amphiphilic homopolymers and copolymers, of acryloylmethylpropanesulfonic acid (AMPS) and/or of acrylamide and/or of acrylic acid and/or of acrylic acid salts or esters; xanthan gum or guar gum; cellulose derivatives; and silicone gums (dimethiconol);

organic screening agents, such as dibenzoylmethane derivatives (including butylmethoxydibenzoylmethane), cinnamic acid derivatives (including ethylhexyl methoxycinnamate), salicylates, para-aminobenzoic acids, β,β'-diphenyl acrylates, benzophenones, benzylidenecamphor derivatives, phenylbenzimidazoles, triazines, phenylbenzotriazoles and anthranilic derivatives;

inorganic screening agents, based on mineral oxides in the form of coated or uncoated pigments or nanopigments, and in particular based on titanium dioxide or zinc oxide;

dyes;

preserving agents;

sequestrants such as EDTA salts;

fragrances;

and mixtures thereof, without this list being limiting.

Examples of such adjuvants are especially mentioned in the CTFA dictionary (International Cosmetic Ingredient Dictionary and Handbook published by The Cosmetic, Toiletry and Fragrance Association, 11th edition, 2006), which describes a wide variety, without limitation, of cosmetic and pharmaceutical ingredients usually used in the skincare industry, that are suitable for use as additional ingredients in the compositions according to the present invention.

The composition may also comprise at least one compound with an optical effect such as fillers, pigments, nacres, tensioning agents and matting polymers, and mixtures thereof.

The term "fillers" should be understood as meaning colorless or white, mineral or synthetic, lamellar or non-lamellar particles suitable for giving the composition body or rigidity and/or softness, a matt effect and uniformity immediately on application. Fillers that may especially be mentioned include talc, mica, silica, kaolin, Nylon® powders such as Nylon-12 (Orgasol® sold by the company Atochem), polyethylene powders, polyurethane powders, polystyrene powders, polyester powders, optionally modified starch, silicone resin microbeads such as those sold by the company Toshiba under the name Tospearl®, hydroxyapatite, and hollow silica microspheres (Silica Beads® from the company Maprecos).

The term "pigments" should be understood as meaning white or colored, mineral or organic particles that are insoluble in the medium, which are intended to color and/or opacify the composition. They may be of standard or nanometric size. Among the mineral pigments that may be mentioned are titanium dioxide, zirconium dioxide and cerium dioxide, and also zinc oxide, iron oxide and chromium oxide.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also colored titanium mica.

The mass concentration in the aqueous phase of these fillers and/or pigments and/or nacres is generally from 0.1% to 20% and preferably from 0.2% to 7% by weight relative to the total weight of the composition.

The term "tensioning agent" should be understood as meaning a compound suitable for making the skin taut and, by means of this tension effect, making the skin smooth and reducing or even immediately eliminating wrinkles and fine lines therefrom. Tensioning agents that may be mentioned include polymers of natural origin. The term "polymer of natural origin" means polymers of plant origin, polymers derived from integuments, egg proteins and latices of natural origin. These polymers are preferably hydrophilic. Polymers of plant origin that may especially be mentioned include proteins and protein hydrolyzates, and more particularly extracts of cereals, of legumes and of oil-yielding plants, such as extracts of corn, of rye, of wheat, of buckwheat, of sesame, of spelt, of pea, of bean, of lentil, of soybean and of lupin. The synthetic polymers are generally in the form of a latex or a pseudolatex and may be of polycondensate type or obtained by free-radical polymerization. Mention may be made especially of polyester/polyurethane and polyether/polyurethane dispersions. Preferably, the tensioning agent is a copolymer of PVP/dimethiconyl acrylate and of hydrophilic polyurethane (Aquamere S-2001® from the company Hydromer).

The term "matting polymers" means herein any polymer in solution, in dispersion or in the form of particles, which reduces the sheen of the skin and which unifies the complexion. Examples that may be mentioned include silicone elastomers; resin particles; and mixtures thereof. Examples of silicone elastomers that may be mentioned include the products sold under the name KSG® by the company Shin-Etsu, under the name Trefil®, BY29® or EPSX® by the company Dow Corning or under the name Gransil® by the company Grant Industries.

The composition used according to the invention may also comprise active agents other than the micro-RNA inhibitor, and in particular at least one active agent chosen from: agents that stimulate the production of growth factors; anti-glycation or deglycating agents; agents that increase collagen synthesis or that prevent its degradation (anti-collagenase agents and especially matrix metalloprotease inhibitors); agents that increase elastin synthesis or prevent its degradation (anti-elastase agents); agents that stimulate the synthesis of integrin or of focal adhesion constituents such as tensin; agents that increase the synthesis of glycosaminoglycans or proteoglycans or that prevent their degradation (anti-proteoglycanase agents); agents that increase fibroblast proliferation; depigmenting or anti-pigmenting agents; antioxidants or free-radical scavengers or anti-pollution agents; and mixtures thereof, without this list being limiting.

Examples of such agents are especially: plant extracts and in particular extracts of *Chondrus crispus*, of *Thermus thermophilus*, of *Pisum sativum* (Proteasyl® TP LS), of *Centella asiatica*, of *Scenedesmus*, of *Moringa pterygosperma*, of witch hazel, of *Castanea sativa*, of *Hibiscus sabdriffa*, of *Polianthes tuberosa*, of *Argania spinosa*, of *Aloe vera*, of *Narcissus tarzetta*, or of liquorice; an essential oil of *Citrus aurantium* (Neroli); α-hydroxy acids such as glycolic acid, lactic acid and citric acid, and esters thereof; β-hydroxy acids such as salicylic acid and derivatives thereof; plant protein hydrolyzates (especially of soybean or of hazelnut); acylated oligopeptides (sold especially by the company Sederma under the trade names Maxilip®, Matrixyl® 3000, Biopeptide® CL or Biopeptide® EL); yeast extracts and in particular of *Saccharomyces cerevisiae*; algal extracts and in particular of laminairia; vitamins and derivatives thereof such as retinyl palmitate, ascorbic acid, ascorbyl glucoside, magnesium or sodium ascorbyl phosphate, ascorbyl palmitate, ascorbyl tetraisopalmitate, ascorbyl sorbate, tocopherol, tocopheryl acetate and tocopheryl sorbate; arbutin; kojic acid; ellagic acid; and mixtures thereof.

As a variant or in addition, the composition used according to the invention may comprise at least one elastase inhibitor (anti-elastase), such as an extract of *Pisum sativum* seeds that is sold especially by the company Laboratoires Sérobiologiques/Cognis France under the trade name Proteasyl TP LS®.

The composition may also contain inert additives or combinations of these additives, such as wetting agents, stabilizers, moisture regulators, pH regulators, osmotic pressure modifiers, or UV-A and UV-B screens.

The following examples illustrate the invention without limiting the scope thereof. These examples are based on the figures listed below:

(A) Human primary keratinocytes were cultured in medium EpiLife with HKGS growth supplements. Cells were culture and serially passaged until the reached the senescent state. The graph is showing the population doublings of primary human keratinocytes during 40 days of culture. After 37 population doublings the growth curve has a plateau, showing that cells stop dividing and are reaching the senescent state.

(B) Cells were collected at the indicated time points to perform western blot analysis for p63, cytokeratin 10 and p16/INK4a. Diminished expression of p63 and increasing levels of p16/INK4a show that cells are entering the replicative senescent state but are not differentiating as show by the undetectability of cytokeratin 10 from the first to the fourth passage. β-actin protein levels are reported as a loading control.

(C) Percentage of proliferating cells is diminishing during senescence as shown by the percentage of BrdU positive primary human keratinocytes at different passages. BrdU incorporation was assessed using the Click-iT technology.

Figure 2:
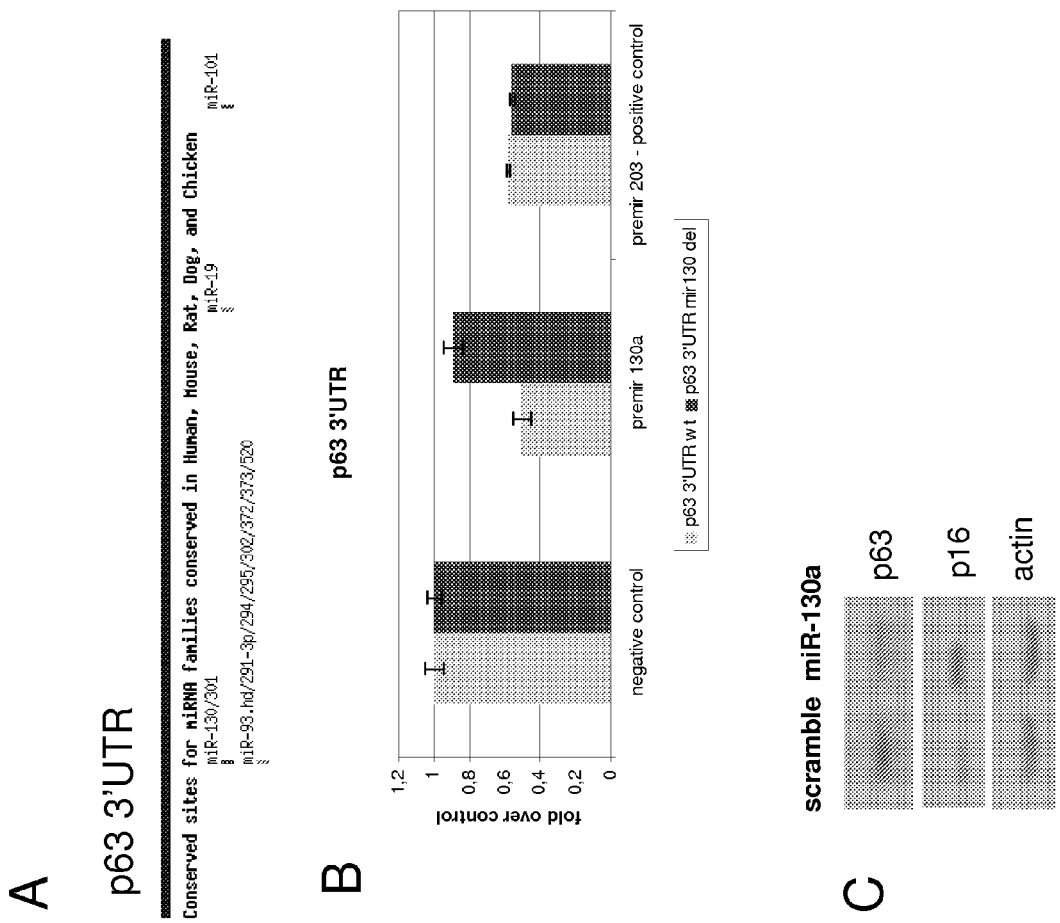

FIG. 2: miR-130a targets p63 mRNA at 3'-UTR (A) A predicted miR-130a target site on p63 3'-UTR was identified by TargetScan 5.1 software.

(B) Insertion of p63 3'-UTR in a luciferase reporter gene leads to diminished luciferase activity in the presence of miR-130a, as additional control cells were transfected with miR-203.

(C) Western blot indicating that ΔNp63 protein is markedly diminished in human keratinocytes transfected pre-miR-130a versus human keratinocytes transfected with a scrambled sequence. As a consequence of miR-130a overexpression, keratinocytes overexpressing miR-130a show an increase in p16/INK4a expression, a marker of cellular senescence. β-actin protein levels are reported as a loading control.

Figure 3:
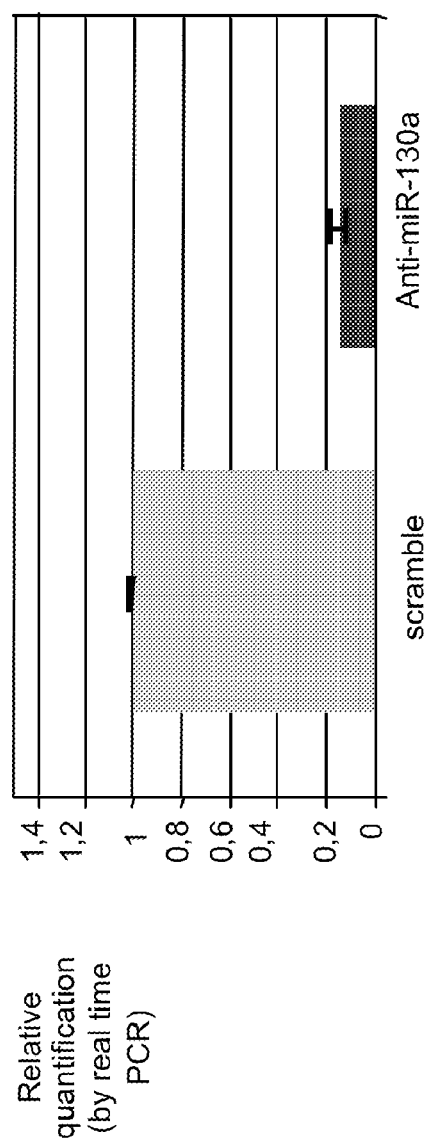

FIG. 3: Modulation of miR-130a by synthetic compounds

Primary human keratinocytes were plated in EpiLife with HKGS growth supplements and treated with several compounds at different concentrations. After 48 hours cells were harvested for relative quantification of miR-130a levels using Real time PCR. The tested compound is significantly downregulating miR-130a levels with respect to the untreated cells.

Figure 4:
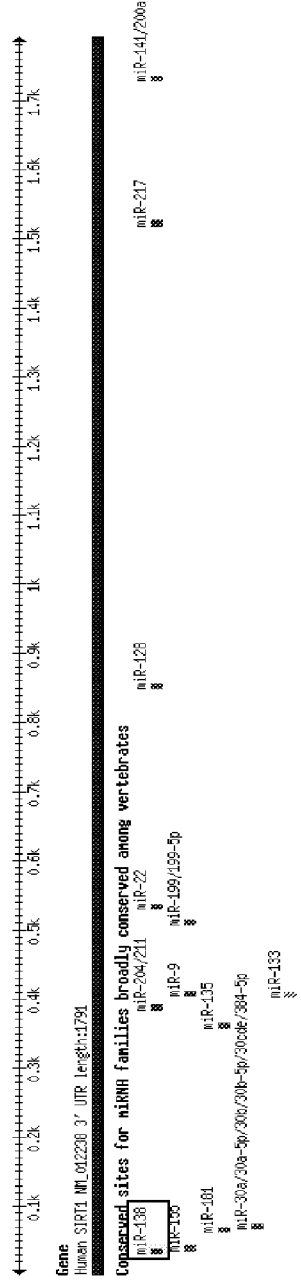
Figure 4:
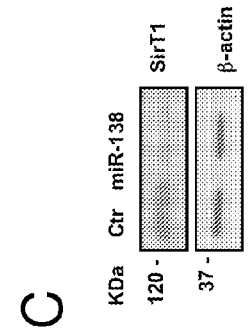
Figure 4:
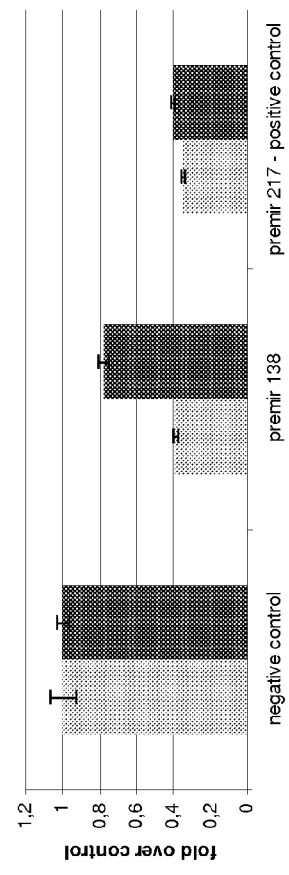

FIG. 4: miR-138 targets Sirt-1 mRNA at 3'-UTR (A) A predicted miR-138 target site on Sirt-1 3'-UTR was identified by TargetScan 5.1 software. (B) Insertion of Sirt-1 3'-UTR in a luciferase reporter gene leads to diminished luciferase activity in the presence of miR-138. MiR-217 was used as positive control. (C) Western blot indicating that SirT-1 protein is markedly diminished in human keratinocytes transfected pre-miR-138 versus human keratinocytes transfected with a scrambled sequence (Ctrl). β-actin protein levels are reported as a loading control.

Figure 5:
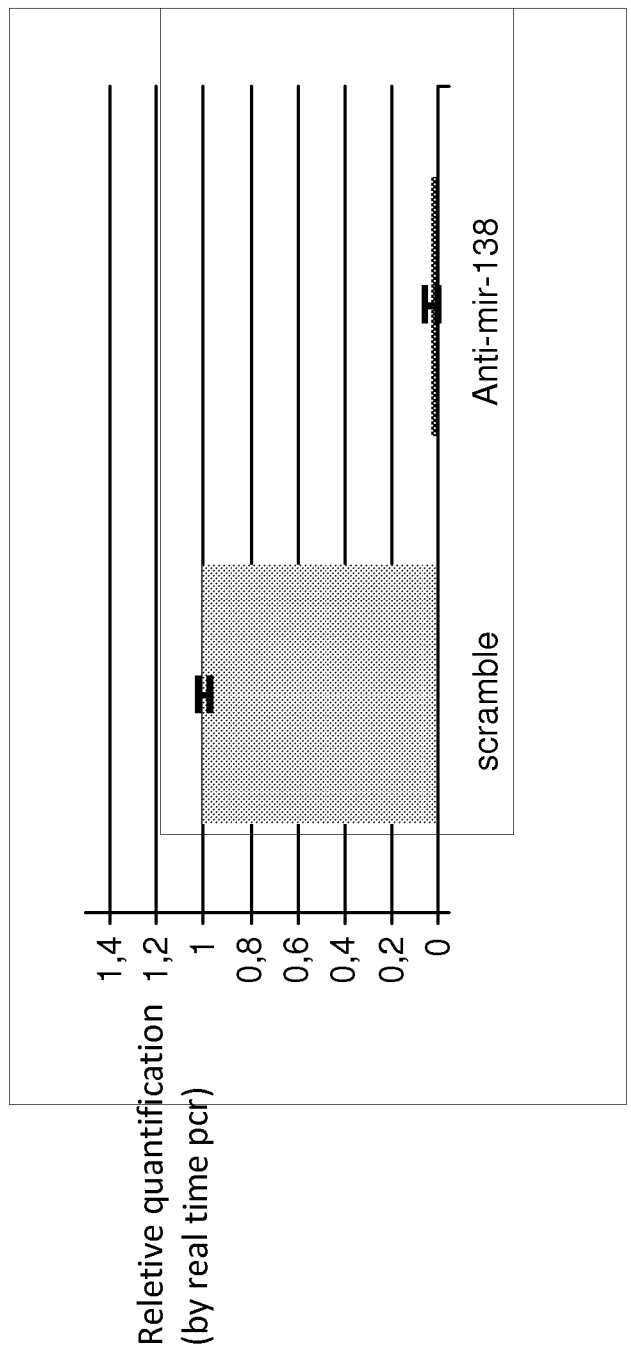

FIG. 5: Modulation of miR-138 by anti-miR-138

Primary human keratinocytes were plated in EpiLife with HKGS growth supplements and transfected with anti-miR-138 (Ambion). After 48 hours cells were harvested for relative quantification of miR-138 levels using Real time PCR. The anti-miR-138 is significantly downregulating miR-138 levels with respect to scramble-transfected cells.

Figure 6:
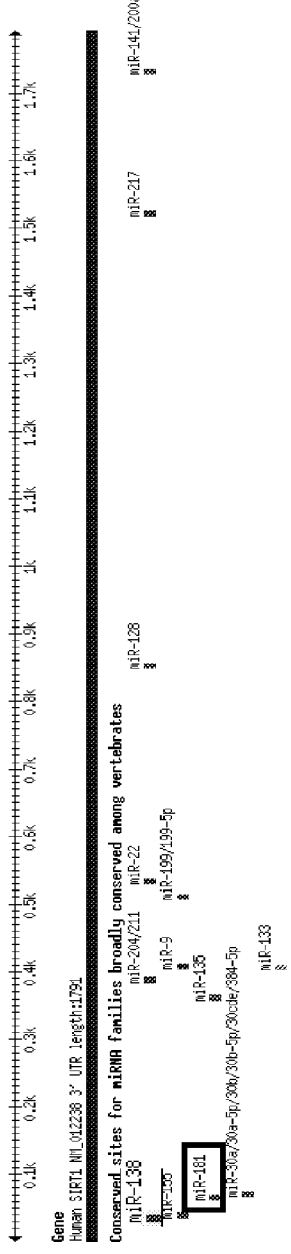
Figure 6:
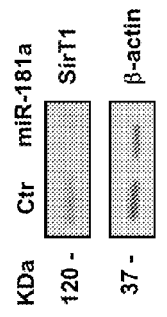
Figure 6:
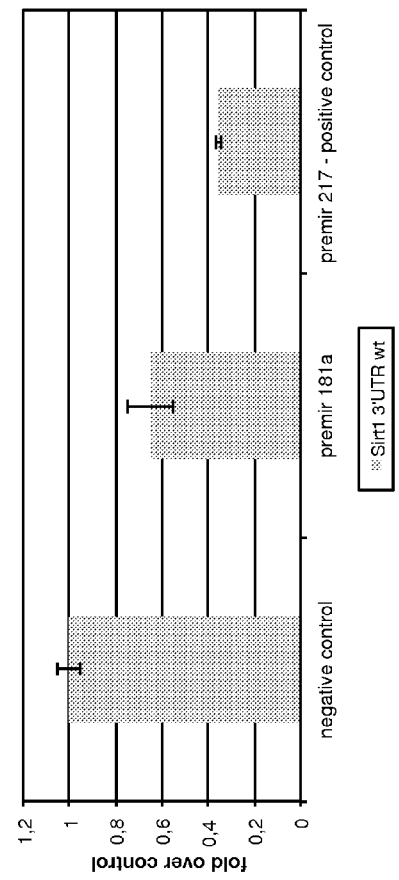

FIG. 6: miR-181a targets Sirt-1 mRNA at 3'-UTR (A) A predicted miR-181a target site on Sirt-1 3'-UTR was identified by TargetScan 5.1 software. (B) Insertion of Sirt-1 3'-UTR in a luciferase reporter gene leads to diminished luciferase activity in the presence of miR-181a. MiR-217 was used as positive control. (C) Western blot indicating that SirT-1 protein is markedly diminished in human keratinocytes transfected pre-miR-181a versus human keratinocytes transfected with a scrambled sequence (Ctrl). β-actin protein levels are reported as a loading control.

Figure 7:
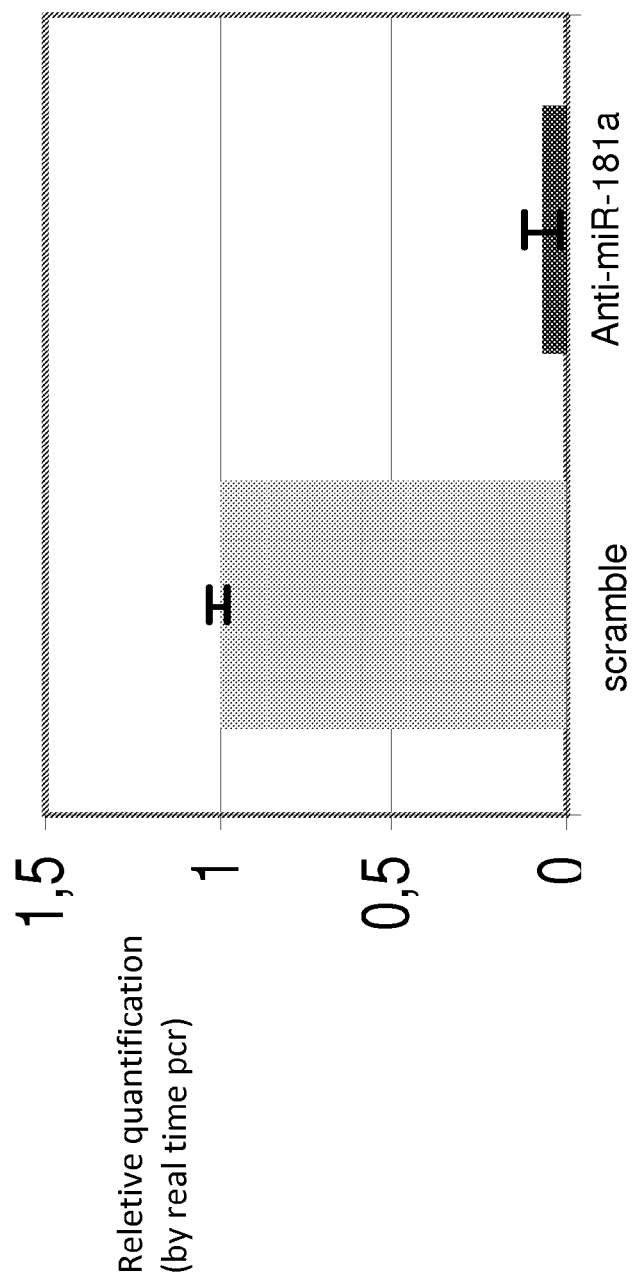

FIG. 7: Modulation of miR-181a by anti-miR-181a

Primary human keratinocytes were plated in EpiLife with HKGS growth supplements and transfected with anti-miR-181a (Ambion). After 48 hours cells were harvested for relative quantification of miR-181a levels using Real time PCR. The anti-miR-181a is significantly downregulating miR-181a levels with respect to scramble-transfected cells.

Figure 8:
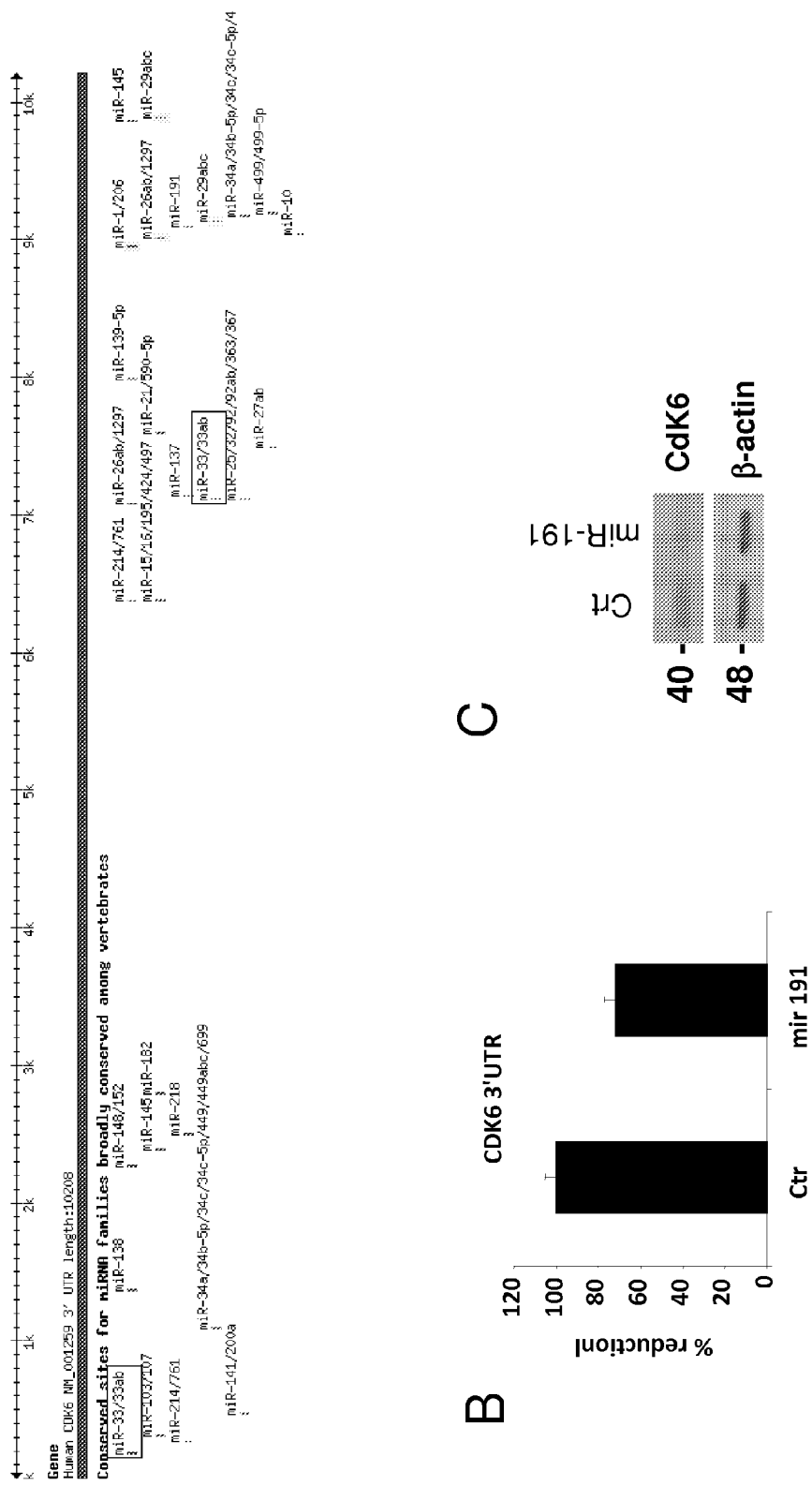

FIG. 8: miR-191 targets CDK6 mRNA at 3'-UTR (A) A predicted miR-191 target site on CDK6 3'-UTR was identified by TargetScan 5.1 software. (B) Insertion of CDK6 3'-UTR in a luciferase reporter gene leads to diminished luciferase activity in the presence of miR-191. (C) Western blot indicating that CDK6 protein is markedly diminished in human keratinocytes transfected pre-miR-1891 versus human keratinocytes transfected with a scrambled sequence (Ctrl). β-actin protein levels are reported as a loading control.

Figure 9:
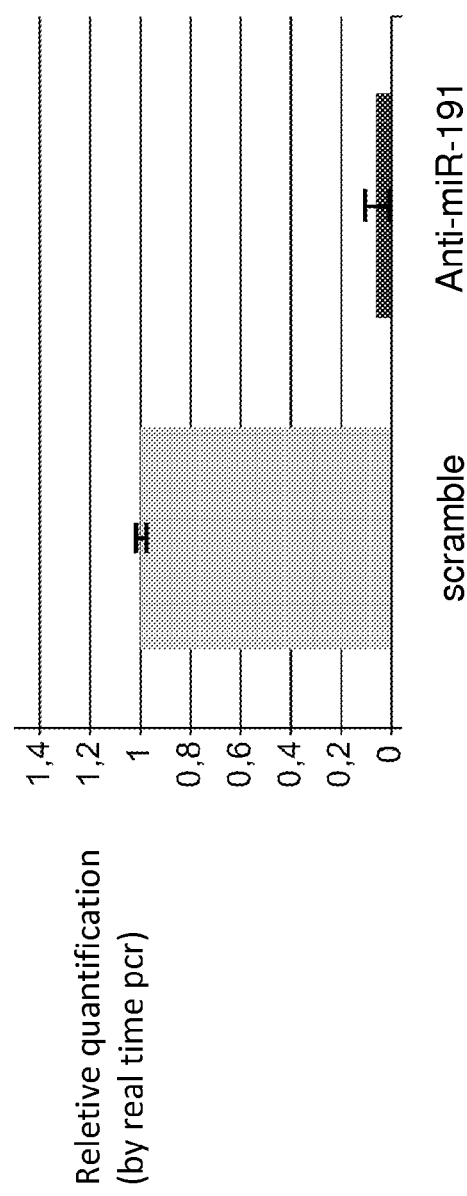

FIG. 9: Modulation of miR-191 by anti-miR-191

Primary human keratinocytes were plated in EpiLife with HKGS growth supplements and transfected with anti-miR-191 (Ambion). After 48 hours cells were harvested for relative quantification of miR-191 levels using Real time PCR.

The anti-miR-191 is significantly downregulating miR-191 levels with respect to scramble-transfected cells.

Figure 10:
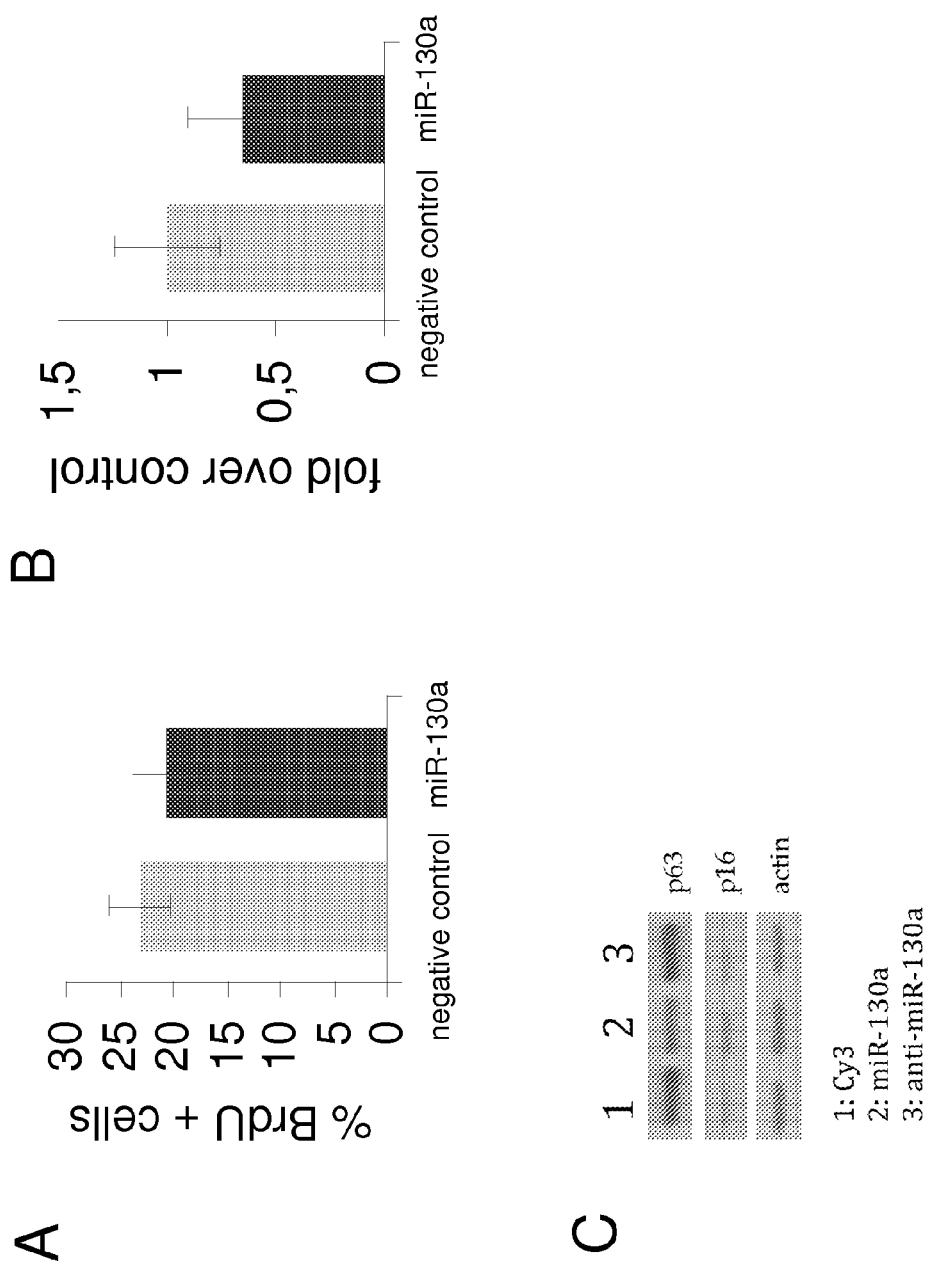

FIG. 10: Over-expression of miR130a in proliferating keratinocytes inhibits p63 protein levels but there is not a significant effect on proliferation and induction of cellular senescence in vitro (A) Upon miR130a overexpression no effects were detected on proliferation and senescence.

(B) This is confirmed as evaluated by BrdU incorporation and SA-β-galactosidase staining. These results are due to the fact that miR-130a, in this specific in vitro conditions, is not able to inhibit p63 at high level. Being p63 still expressed in the cells as observed in (C), we can not detect the effects on proliferation and senescence.

Figure 11:
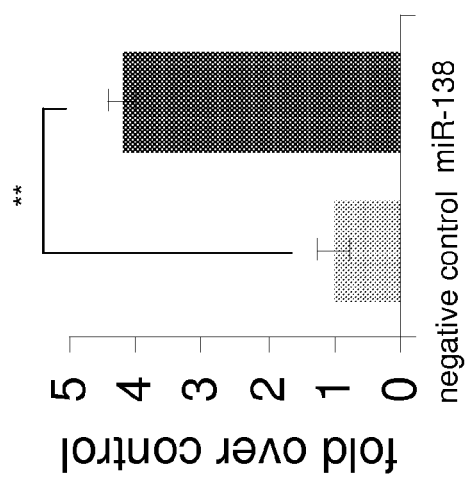
Figure 11:
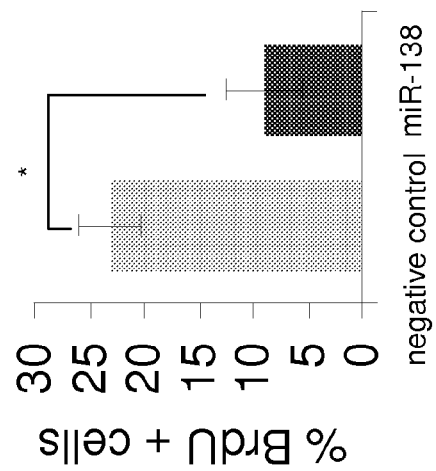

FIG. 11: Over-expression of miR138 in proliferating keratinocytes inhibits proliferation and induces cellular senescence (A) Upon miR138 overexpression, proliferation is significantly diminished as evaluated by BrdU incorporation.

(B) Evaluation of senescence by the staining for SA-β-galactosidase shows a significantly increase upon miR-138 transfection (±s.d. *p-value<0.01, **p-value<0.005 by Student t test).

Figure 12:
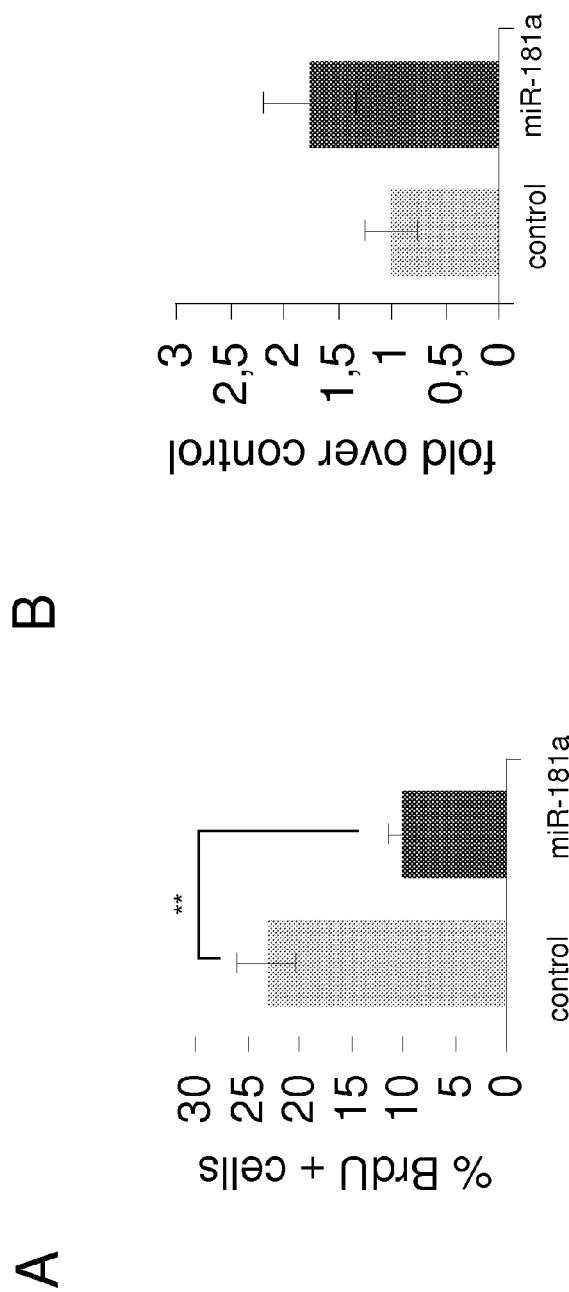

FIG. 12: Over-expression of miR181a in proliferating keratinocytes inhibits proliferation and induces cellular senescence (A) Upon miR181a overexpression proliferation is significantly diminished as evaluated by BrdU incorporation.

(B) Evaluation of senescence by the staining for SA-β-galactosidase shows a significantly increase upon miR-181a transfection (±s.d. *p-value<0.01, **p-value<0.005 by Student t test).

Figure 13:
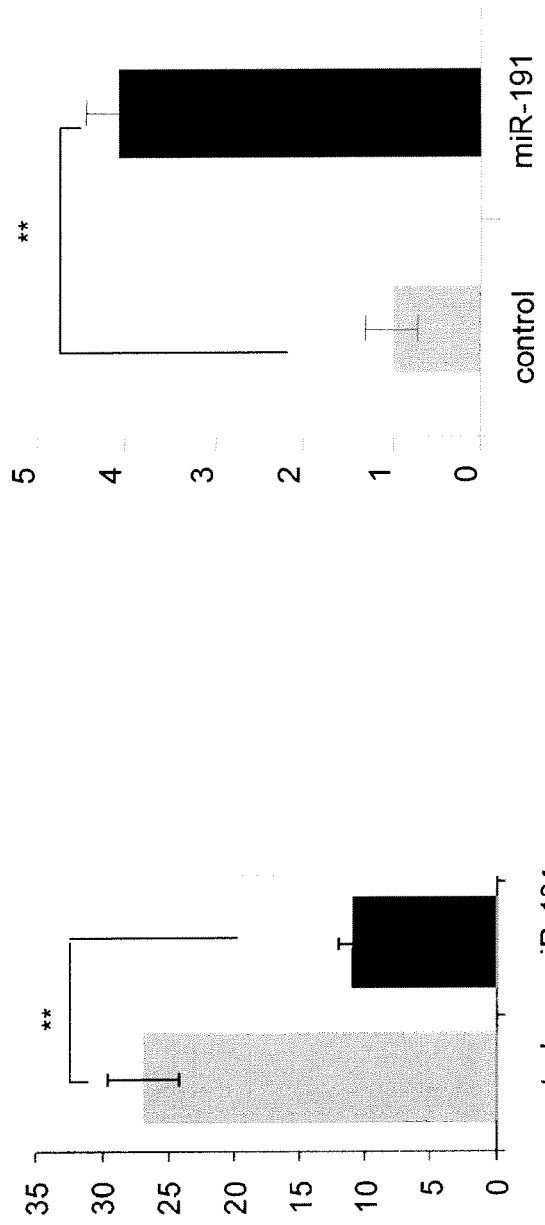

FIG. 13: Over-expression of miR191 in proliferating keratinocytes inhibits proliferation and induces cellular senescence (A) Upon miR191 overexpression proliferation is significantly diminished as evaluated by BrdU incorporation.

(B) Evaluation of senescence by the staining for SA-β-galactosidase shows a significantly increase upon miR-191 transfection (±s.d. **p-value<0.005 by Student t test).

Figure 14:
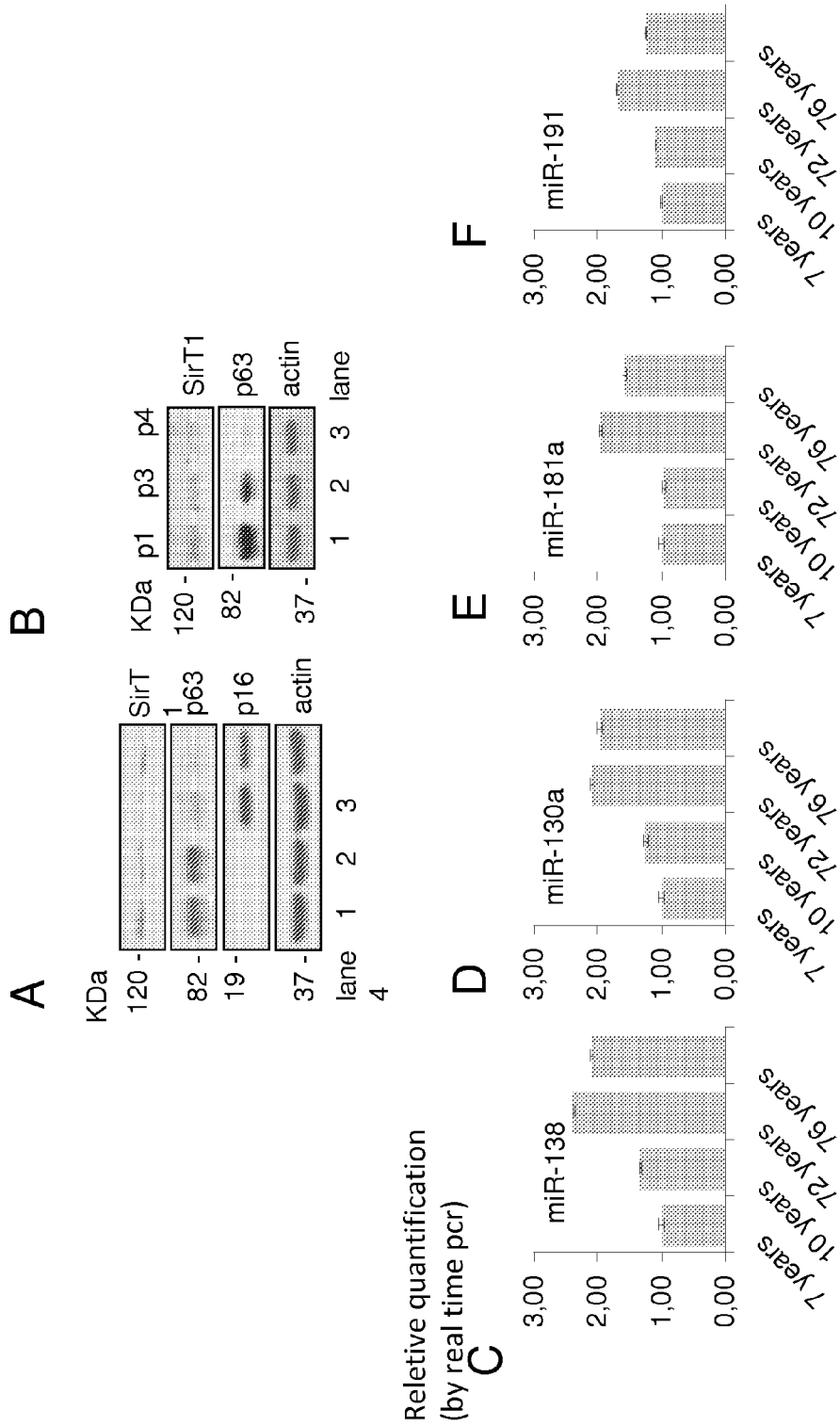

FIG. 14: Selected miRs upregulated during senescence are also upregulated in in vivo aged skin (A) Skin biopsies were taken from patients at the following ages: lane 1=7 years; lane 2=10 years; lane 3=70 years and lane 4=76 years. Western blots showing that p16, SirT1 and p63 behave in human skin like in the in vitro replicative senescence model (B) are shown. (C-F) RT-PCR of selected miRs levels in differently aged human skin.

EXAMPLE 1

Construction of a Model of Senescent Keratinocytes

Material and Methods
Cell Culture and Transfection

Neonatal Human Primary Epidermal Keratinocytes (Hekn, Cascade, Invitrogen, Carlsbad, Calif., USA) were cultured in EpiLife medium added with HKGS growth supplements (Cascade). Cells were constantly kept subconfluent in order to avoid triggering of a differentiation process. Cells were passaged usually once a week, at each passage the harvested cells number and seeded cell number were recorded in order to calculate the population doublings occurring between passages and the population doubling time. At each passage different aliquots of the cells were harvested to extract in triplicate RNA and proteins and an aliquot was submitted to senescence activated β-galactosidase staining in order to assay the senescent or non-senescent state of the cells.

Senescence-Associated β-Galactosidase Staining

Cells were grown in 6-well culture plates, washed with PBS, and fixed with 2% formaldehyde/0.2% glutaraldehyde in PBS for 5 minutes. After another washing step with PBS, cells were incubated with β-galactosidase staining solution (150 mmol/L NaCl, 2 mmol/L MgCl2, 5 mmol/L potassium ferricyanide, 5 mmol/L potassium ferrocyanide, 40 mmol/L citric acid, 12 mmol/L sodium phosphate, pH 6.0, containing 1 mg/mL 5-bromo-4-chloro-3-indolyl-β-Dgalactoside [X-gal]) for 24 hours at 37° C. The reaction was stopped by replacing the staining solution with 70% glycerol.

Cell Proliferation and Cell Cycle Analysis

Methods used to evaluate cell proliferation are generally based on incorporation of thymidine analogues such as bromodeoxyuridine (BrdU) during DNA synthesis. The Click-iT™ EdU flow cytometry assay kit is a novel alternative to BrdU assay (Molecular Probes, Eugene, Oreg., USA). This method replaces antibody-based detection of the nucleoside analogue, BrdU, with EdU (5-ethynyl-2'-deoxyuridine), which is a nucleoside analogue of thymidine that is incorporated into DNA during active DNA synthesis. Briefly, cells were incubated with EdU for 4 hrs. After incubation, samples were fixed, permeabilized and stained according to the manufacturer's protocol. Cell cycle was analysed using a FACS-Calibur flow cytometer (BD Biosciences, San Jose, Calif., USA). Fifteen thousand events were evaluated using the Cell Quest (BD) and Modfit LT (Verity Software; BD) programs.

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA).

anti-p63 (Ab4, Neomarkers, Fremont, Calif., USA; 1/500 dilution), polyclonal anti-K10 (Covance, Princeton, N.J., USA; 1/1000 dilution), anti-β actin (Sigma, St Louis, Minn., USA; 1/5000 dilution), anti-p16 (Santa Cruz Biotechnology, California, USA; dilution 1:1000), were used.

Results

Figure 1:
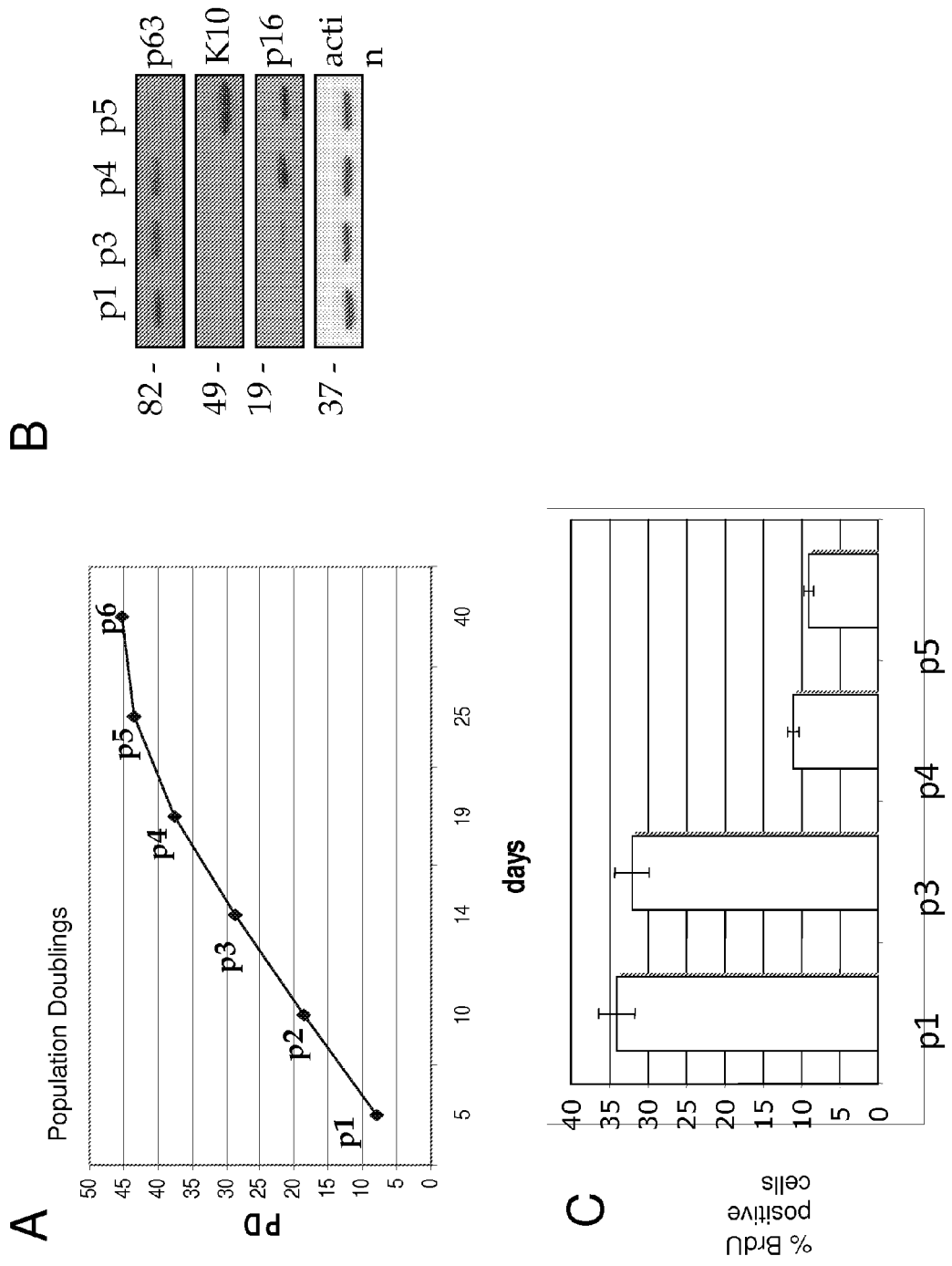
FIG. 1: Establishment of a model for replicative senescence in primary human neonatal keratinocytes ("pre-senescent keratinocytes")

Establishment of a Model for Replicative Senescence in Primary Human Neonatal Keratinocytes Human primary keratinocytes were cultured in medium EpiLife with HKGS growth supplements. Cells were culture and serially passaged until the reached the senescent state. FIG. 1A is showing the population doublings of primary human keratinocytes during 40 days of culture. After 37 population doublings the growth curve has a plateau, showing that cells stop dividing and are reaching the senescent state.

Cells were collected at p1, p3, p4 and p5 to perform western blot analysis for p63, cytokeratin 10 (K10) and p16/INK4a. Diminished expression of p63 and increasing levels of p16/INK4a show that cells are entering into the replicative senescent state but are not differentiating as shown by the absence of cytokeratin 10 from the first to the fourth passage. β-actin protein levels are reported as a loading control.

Primary human keratinocytes undergo replicative senescence after the fourth passage at 37 population doublings. Staining of SA-β-galactosidase staining in primary human keratinocytes at different passages show the expression of the senescent marker in older cells (p4).

Percentage of proliferating cells is diminishing during senescence as shown by the percentage of BrdU positive primary human keratinocytes at different passages. BrdU incorporation was assessed using the Click-iT technology. The cells hereby obtained are a model for senescent keratinocytes, and are called pre-senescent keratinocytes.

EXAMPLE 2

Expression of miR-130a During Keratinocyte Induced Senescence

Material and Methods
Cell Culture and Transfection

The human primary keratinocytes described in Example 1 are used in this example.

Human primary keratinocytes were cultured in EpiLife medium with HKGS growth supplements (Cascade) and treated with CaCl2 1.2 mM in order to induce the differentiation process. Differentiated cells were harvested after 7 days of treatment for microRNA levels analysis. Human primary keratinocytes were transfected with human pre-miR-130a, anti-miR-130a and Cy3-labeled negative control (Ambion, Texas, USA) using the SiPORT neoFX transfection agent (Ambion) according to manufacturer protocols. 16 hrs after transfection, the medium was removed and replaced with fresh medium.

800.000 human primary keratinocytes were plated in EpiLife with HKGS growth supplements and treated with test compounds. After 48 hours cells were harvested for microRNA levels analysis. HEK 293E cells were grown in D-MEM High glucose with 10% FBS, 100 U penicillin, 100 µg streptomycin (GIBCO, Invitrogen).

HEK 293E cells were transfected by Lipofectamine 2000 according to manufacturer protocols (Invitrogen). Hekn cells were treated with the test compounds for 48 hrs. Cells were collected and mRNA extracted following standard procedures. Real time PCR were performed as described below.

RNA Extraction and Real Time PCR Analysis

Total RNA from cells or tissue was isolated using mirVana mirRNA Isolation Kit (Ambion) by following the manufacturer's protocol for total RNA extraction. Total RNA was quantified using a NanoDrop Spectophotometer (Thermo Scientific, Delaware, USA) and RNA quality was controlled on an agarose gel. For microRNA detection, RNA was reverse transcribed using TaqMan MicroRNA Reverse Transcription kit and qRT-PCR was performed with TaqMan universal master mix (Applied Biosystem) and specific primers for miR-130a. U18 was used as an internal control (Applied Biosystem). The expression of each gene and miR was defined from the threshold cycle (Ct), and relative expression levels were calculated by using the 2-ΔΔCt method after normalization with reference to the expression of the housekeeping gene U18.

Senescence-Associated β-Galactosidase Staining

Cells were grown in 6-well culture plates, washed with PBS, and fixed with 2% formaldehyde/0.2% glutaraldehyde in PBS for 5 minutes. After another washing step with PBS, cells were incubated with β-galactosidase staining solution (150 mmol/L NaCl, 2 mmol/L MgCl2, 5 mmol/L potassium ferricyanide, 5 mmol/L potassium ferrocyanide, 40 mmol/L citric acid, 12 mmol/L sodium phosphate, pH 6.0, containing 1 mg/mL 5-bromo-4-chloro-3-indolyl-β-Dgalactoside [X-gal]) for 24 hours at 37° C. The reaction was stopped by replacing the staining solution with 70% glycerol.

Cell Proliferation and Cell Cycle Analysis

Methods used to evaluate cell proliferation are generally based on incorporation of thymidine analogues such as bromodeoxyuridine (BrdU) during DNA synthesis. The Click-iT™ EdU flow cytometry assay kit is a novel alternative to BrdU assay (Molecular Probes, Eugene, Oreg., USA). This method replaces antibody-based detection of the nucleoside analogue, BrdU, with EdU (5-ethynyl-2'-deoxyuridine), which is a nucleoside analogue of thymidine that is incorporated into DNA during active DNA synthesis. Briefly, cells were incubated with EdU for 4 hrs. After incubation, samples were fixed, permeabilized and stained according to the manufacturer's protocol. Cell cycle was analysed using a FACS-Calibur flow cytometer (BD Biosciences, San Jose, Calif., USA). Fifteen thousand events were evaluated using the Cell Quest (BD) and Modfit LT (Verity Software; BD) programs.

Constructs

Human p63 3'UTR was amplified by PCR from the first nucleotide after stop codon to the last nucleotide before polyadenylation signal from human genomic DNA using the following primers:

```
p63UTR-SpeIF
                                          SEQ ID NO: 5
5'- GGCCACTAGTGCCTCACCATGTGAGCTCTTC -3';

p63UTR-SpeIR
                                          SEQ ID NO: 6
5'- GGCCACTAGTGCATGTCCTGGCAAACAAAAAGAG -3'.
```

The 2770 bp fragment (i.e. p63 3'UTR wt), after SpeI restriction, was ligated to a compatible XbaI linearized pGL3 Control vector (Promega, Madison, Wis., USA).

On the other hand, from this wild type sequence, the miR-130a predicted target site (7 bp, UUGCACU) was deleted by PCR using the following overlapping primers:

```
Del130F
                                          SEQ ID NO: 7
5'- TTAAATGAAAGAAAATTGAGTATTGACCATTTTTTAATT -3';

Del130R
                                          SEQ ID NO: 8
5'- AATTAAAAAATGGTCAATACTCAATTTTCTTTCATTTAA -3'.
```

Therefore, the p63 3'UTR miR-130a del is obtained.

Bioinformatics

Analysis of miR-130a target sites on p63 3'UTR were performed using the TargetScan 5.1 software available at http://www.targetscan.org/

Luciferase Assay

2×10⁵ HEK 293E cells were seeded in 12 well dishes 24 hours before transfection. Cells were transfected using Lipofectamine 2000 (Invitrogen) with 100 ng of pGL3 vectors (i.e. with p63 3'UTR wt or p63 3'UTR miR-130a del), 12 pmol of pre-miR-130a or pre-miR scramble sequence (Ambion), and 10 ng of *Renilla* luciferase pRL-CMV vector. Luciferase activities of cellular extracts were measured 24 hours after transfection, by using a Dual Luciferase Reporter Assay System (Promega); light emission was measured over 10 seconds using an OPTOCOMP I luminometer. Efficiency of transfection was normalised using *Renilla* luciferase activity.

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA).

anti-p63 (Ab4, Neomarkers, Fremont, Calif., USA; 1/500 dilution), anti-β actin (Sigma, St Louis, Minn., USA; 1/5000 dilution), anti-p16 (Santa Cruz Biotechnology, California, USA; dilution 1:1000) were used.

Results miR-130a Levels in Senescing and Differentiating Keratinocytes

At p1 and p4, cells were collected to perform Real time PCR.

Relative quantification of miR-130a levels between p1 and p4 shows significant increase in miR-130a expression in senescent keratinocytes: at p4, miR-130a expression is around 1.48 (±0.08) higher than its expression at p1 (which is equal to 1.00±0.07).

To the contrary, in proliferating keratinocytes, after 7 days of calcium treatment, miR-130a expression is around 0.347 (±0.04), whereas at day 0 it is 1.00 (±0.07).

Therefore, the keratinocyte senescent state, but not the keratinocyte proliferating state, is associated with an increase in miR-130a expression.

miR-130a Targets p63 mRNA at 3'UTR

Bioinformatic analysis show that p63 is a putative miR-130a targets (FIG. 2A). The insertion of p63 3'UTR wt in a luciferase reporter gene leads to diminished luciferase activity in the presence of pre-miR-130a (0.503±0.05 fold over control). Additional control cells were transfected with pre-miR-203 (a known miR targeting p63 3'UTR) as positive control: the luciferase activity in this case is 0.58±0.0096 fold over control (FIG. 2B).

The insertion of p63 3'UTR miR-130a del in a luciferase reporter gene leads to a slightly decreased luciferase activity in the presence of pre-miR-130a (0.89±0.0537 fold over control). Additional control cells transfected with pre-miR-203 show a luciferase activity 0.56±0.013 fold over control (FIG. 2B).

As shown in FIG. 2C, p63 protein is markedly diminished in human keratinocytes transfected with pre-miR-130a versus human keratinocytes transfected with a scrambled sequence. As a consequence of miR-130a overexpression, keratinocytes overexpressing miR-130a show an increase in p16/INK4a expression, a marker of cellular senescence. β-actin protein levels are reported as a loading control.

These results suggest that miR-130a targets p63 mRNA at 3'UTR.

Modulation of miR-130a by Synthetic Compounds

Primary human keratinocytes were plated in EpiLife with HKGS growth supplements and treated with an anti-miR-130a at different concentrations. After 48 hours cells were harvested for relative quantification of miR-130a levels using Real time PCR. The anti-miR-130a is significantly down-regulating miR-130a levels with respect to the untreated cells; the expression of miR-130a in treated cells is only 0.138±0.032 (whereas it is 1.00±0.01 for scramble) (FIG. 3).

EXAMPLE 3

Expression of miR-138 During Keratinocyte Induced Senescence

Material and Methods
Cell Culture and Transfection

The human primary keratinocytes described in Example 1 are used in this example.

Human primary keratinocytes were cultured in EpiLife medium with HKGS growth supplements (Cascade) and treated with CaCl2 1.2 mM in order to induce the differentiation process. Differentiated cells were harvested after 7 days of treatment for microRNA levels analysis. Human primary keratinocytes were transfected with human pre-miR-138, anti-miR-138 and Cy3-labeled negative control (Ambion, Texas, USA) using the SiPORT neoFX transfection agent (Ambion) according to manufacturer protocols. 16 hrs after transfection, the medium was removed and replaced with fresh medium.

800.000 human primary keratinocytes were plated in EpiLife with HKGS growth supplements and treated with the test compounds. After 48 hours cells were harvested for microRNA levels analysis. HEK 293E cells were grown in D-MEM High glucose with 10% FBS, 100 U penicillin, 100 μg streptomycin (GIBCO, Invitrogen).

HEK 293E cells were transfected by Lipofectamine 2000 according to manufacturer protocols (Invitrogen). Hekn cells were treated with the test compounds for 48 hrs. Cells were collected and mRNA extracted following standard procedures. Real time PCR were performed as described below.

RNA Extraction and Real Time PCR Analysis

Total RNA from cells or tissue was isolated using mirVana mirRNA Isolation Kit (Ambion) by following the manufacturer's protocol for total RNA extraction. Total RNA was quantified using a NanoDrop Spectophotometer (Thermo Scientific, Delaware, USA) and RNA quality was controlled on an agarose gel. For microRNA detection, RNA was reverse transcribed using TaqMan MicroRNA Reverse Transcription kit and qRT-PCR was performed with TaqMan universal master mix (Applied Biosystem) and specific primers for miR-138. U18 was used as an internal control (Applied Biosystem). The expression of each gene and miR was defined from the threshold cycle (Ct), and relative expression levels were calculated by using the 2-ΔΔCt method after normalization with reference to the expression of the housekeeping gene U18.

Senescence-Associated β-Galactosidase Staining

Cells were grown in 6-well culture plates, washed with PBS, and fixed with 2% formaldehyde/0.2% glutaraldehyde in PBS for 5 minutes. After another washing step with PBS, cells were incubated with β-galactosidase staining solution (150 mmol/L NaCl, 2 mmol/L MgCl2, 5 mmol/L potassium ferricyanide, 5 mmol/L potassium ferrocyanide, 40 mmol/L citric acid, 12 mmol/L sodium phosphate, pH 6.0, containing 1 mg/mL 5-bromo-4-chloro-3-indolyl-β-Dgalactoside [X-gal]) for 24 hours at 37° C. The reaction was stopped by replacing the staining solution with 70% glycerol.

Cell Proliferation and Cell Cycle Analysis

Methods used to evaluate cell proliferation are generally based on incorporation of thymidine analogues such as bromodeoxyuridine (BrdU) during DNA synthesis. The Click-iT™ EdU flow cytometry assay kit is a novel alternative to BrdU assay (Molecular Probes, Eugene, Oreg., USA). This method replaces antibody-based detection of the nucleoside analogue, BrdU, with EdU (5-ethynyl-2'-deoxyuridine), which is a nucleoside analogue of thymidine that is incorporated into DNA during active DNA synthesis. Briefly, cells were incubated with EdU for 4 hrs. After incubation, samples were fixed, permeabilized and stained according to the manufacturer's protocol. Cell cycle was analysed using a FACS-Calibur flow cytometer (BD Biosciences, San Jose, Calif., USA). Fifteen thousand events were evaluated using the Cell Quest (BD) and Modfit LT (Verity Software; BD) programs.

Constructs

Human Sirt-1 3'UTR was amplified by PCR from the first nucleotide after stop codon to the last nucleotide before polyadenylation signal from human genomic DNA using the following primers:

```
pSirT1UTR-StyIF
                                       SEQ ID NO: 9
5'- GACCCTAGGAGATGATCAAGAGGC -3';

pSirT1UTR-StyIR
                                       SEQ ID NO: 10
5'- GCCTAGGAAGCTGTACAAATTGCT -3'.
```

The 1940 bp fragment (i.e. pSirT1 3'UTR wt), after SpeI restriction, was ligated to a compatible XbaI linearized pGL3 Control vector (Promega, Madison, Wis., USA).

On the other hand, from this wild type sequence, the miR-138 predicted target site (7 bp, CACCAGCA) was deleted by PCR using the following overlapping primers:

```
Del138F
                                       SEQ ID NO: 11
5'- GCAGGTACAGGAATTGTTCCTTAGGAACTTTAGCATGTC-3';

Del138R
                                       SEQ ID NO: 12
5'- GACATGCTAAAGTTCCTAAGGAACAATTCCTGTACCTGC -3'.
```

Therefore, the SirT1 3'UTR miR-138 del is obtained.

Bioinformatics

Analysis of miR-138 target sites on Sirt-1 3'UTR were performed using the TargetScan 5.1 software available at http://www.targetscan.org/

Luciferase Assay $2 \times 10^5$ HEK 293E cells were seeded in 12 well dishes 24 hours before transfection. Cells were transfected using Lipofectamine 2000 (Invitrogen) with 100 ng of pGL3 vectors (i.e. with Sirt-1 3'UTR wt or Sirt-1 3'UTR miR-138 del), 12 pmol of pre-miR-138 or pre-miR scramble sequence (Ambion), and 10 ng of *Renilla* luciferase pRL-CMV vector. Luciferase activities of cellular extracts were measured 24 hours after transfection, by using a Dual Luciferase Reporter Assay System (Promega); light emission was measured over 10 seconds using an OPTOCOMP I luminometer. Efficiency of transfection was normalised using *Renilla* luciferase activity.

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA).

anti-Sirt-1 (Abcam, Cambridge, United Kingdom; 1/500 dilution), anti-β actin (Sigma, St Louis, Minn., USA; 1/5000 dilution), were used.

Results miR-138 Levels in Senescing and Differentiating Keratinocytes

At p1 and p4, cells were collected to perform Real time PCR. Relative quantification of miR-138 levels between p1 and p4 shows significant increase in miR-138 expression in senescent keratinocytes: at p4, miR-138 expression is around 2.76 (±0.06) higher than its expression at p1 (which is equal to 1.00±0.05).

To the contrary, in proliferating keratinocytes, after 7 days of calcium treatment, miR-138 expression is around 0.21 (±0.02), whereas at day 0 it is 1.00 (±0.02).

Therefore, the keratinocyte senescent state, but not the keratinocyte proliferating state, is associated with an increase in miR-138 expression.

miR-138 Targets Sirt-1 mRNA at 3'UTR

Bioinformatic analysis show that SirT1 is a putative miR-138 targets (FIG. 4A). The insertion of Sirt-1 3'UTR wt in a luciferase reporter gene leads to diminished luciferase activity in the presence of pre-miR-138 (0.39±0.014 fold over control). Additional control cells were transfected with pre-miR-217 (a known miR targeting Sirt-1 3'UTR) as positive control: the luciferase activity in this case is 0.35±0.009 fold over control (FIG. 4B).

The insertion of Sirt-1 3'UTR miR-138 del in a luciferase reporter gene leads to a slightly decreased luciferase activity in the presence of pre-miR-138 (0.78±0.03 fold over control). Additional control cells transfected with pre-miR-217 show a luciferase activity 0.4±0.008 fold over control (FIG. 4B). As shown in FIG. 4C, SirT1 protein is markedly diminished in human keratinocytes transfected with pre-miR-138 versus human keratinocytes transfected with a scrambled sequence (Ctrl). β-actin protein levels are reported as a loading control. These data demonstrate that SirT1 is a miR-138 target.

Modulation of miR-138 by Synthetic Compounds

Primary human keratinocytes were plated in EpiLife with HKGS growth supplements and treated with an anti-miR-138 at different concentrations. After 48 hours cells were harvested for relative quantification of miR-138 levels using Real time PCR. The anti-miR-138 is significantly downregulating miR-138 levels with respect to the untreated cells; the expression of miR-138 in treated cells is only 0.032±0.026 (FIG. 5).

EXAMPLE 4

Expression of miR-181a During Keratinocyte Induced Senescence

Material and Methods

Cell Culture and Transfection

The human primary keratinocytes described in Example 1 are used in this example. Human primary keratinocytes were cultured in EpiLife medium with HKGS growth supplements (Cascade) and treated with CaCl2 1.2 mM in order to induce the differentiation process. Differentiated cells were harvested after 7 days of treatment for microRNA levels analysis. Human primary keratinocytes were transfected with human pre-miR-181a, anti-miR-181a and Cy3-labeled negative control (Ambion, Texas, USA) using the SiPORT neoFX transfection agent (Ambion) according to manufacturer protocols. 16 hrs after transfection, the medium was removed and replaced with fresh medium.

800.000 human primary keratinocytes were plated in EpiLife with HKGS growth supplements and treated with test compounds. After 48 hours cells were harvested for microRNA levels analysis. HEK 293E cells were grown in D-MEM High glucose with 10% FBS, 100 U penicillin, 100 μg streptomycin (GIBCO, Invitrogen).

HEK 293E cells were transfected by Lipofectamine 2000 according to manufacturer protocols (Invitrogen). Hekn cells were treated with the test compounds for 48 hrs. Cells were collected and mRNA extracted following standard procedures. Real time PCR were performed as described below.

RNA Extraction and Real Time PCR Analysis

Total RNA from cells or tissue was isolated using mirVana mirRNA Isolation Kit (Ambion) by following the manufacturer's protocol for total RNA extraction. Total RNA was quantified using a NanoDrop Spectophotometer (Thermo Scientific, Delaware, USA) and RNA quality was controlled on an agarose gel. For microRNA detection, RNA was reverse transcribed using TaqMan MicroRNA Reverse Transcription kit and qRT-PCR was performed with TaqMan universal master mix (Applied Biosystem) and specific primers for miR-181a. U18 was used as an internal control (Applied Biosystem). The expression of each gene and miR was defined from the threshold cycle (Ct), and relative expression levels were calculated by using the 2-ΔΔCt method after normalization with reference to the expression of the housekeeping gene U18.

Senescence-Associated β-Galactosidase Staining

Cells were grown in 6-well culture plates, washed with PBS, and fixed with 2% formaldehyde/0.2% glutaraldehyde in PBS for 5 minutes. After another washing step with PBS, cells were incubated with β-galactosidase staining solution (150 mmol/L NaCl, 2 mmol/L MgCl2, 5 mmol/L potassium ferricyanide, 5 mmol/L potassium ferrocyanide, 40 mmol/L citric acid, 12 mmol/L sodium phosphate, pH 6.0, containing 1 mg/mL 5-bromo-4-chloro-3-indolyl-β-Dgalactoside [X-gal]) for 24 hours at 37° C. The reaction was stopped by replacing the staining solution with 70% glycerol.

Cell Proliferation and Cell Cycle Analysis

Methods used to evaluate cell proliferation are generally based on incorporation of thymidine analogues such as bromodeoxyuridine (BrdU) during DNA synthesis. The Click-iT™ EdU flow cytometry assay kit is a novel alternative to BrdU assay (Molecular Probes, Eugene, Oreg., USA). This method replaces antibody-based detection of the nucleoside analogue, BrdU, with EdU (5-ethynyl-2'-deoxyuridine), which is a nucleoside analogue of thymidine that is incorporated into DNA during active DNA synthesis. Briefly, cells were incubated with EdU for 4 hrs. After incubation, samples were fixed, permeabilized and stained according to the manufacturer's protocol. Cell cycle was analysed using a FACS-Calibur flow cytometer (BD Biosciences, San Jose, Calif., USA). Fifteen thousand events were evaluated using the Cell Quest (BD) and Modfit LT (Verity Software; BD) programs.

Constructs

Human Sirt-1 3'UTR was amplified by PCR from the first nucleotide after stop codon to the last nucleotide before polyadenylation signal from human genomic DNA using the following primers:

```
pSirT1UTR-StyIF
                                SEQ ID NO: 13
5'- GACCCTAGGAGATGATCAAGAGGC -3';

pSirT1UTR-StyIR
                                SEQ ID NO: 14
5'- GCCTAGGAAGCTGTACAAATTGCT -3'.
```

The 1940 bp fragment (i.e. pSirT1 3'UTR wt), after SpeI restriction, was ligated to a compatible XbaI linearized pGL3 Control vector (Promega, Madison, Wis., USA).

On the other hand, from this wild type sequence, the miR-181a predicted target site (7 bp, UGAAUGU) was deleted by PCR using the following overlapping primers:

```
Del181aF
                                SEQ ID NO: 15
5'-GGAACTTTAGCATGTCAAAATTACTTGTGAACTCGATAGA-3';

Del181aR
                                SEQ ID NO: 16
5'-TCTATCGAGTTCACAAGTAATTTTGACATGCTAAAGTTCC-3'.
```

Therefore, the SirT1 3'UTR miR-181a del is obtained.

Bioinformatics

Analysis of miR-181a target sites on Sirt-1 3'UTR were performed using the TargetScan 5.1 software available at http://www.targetscan.org/

Luciferase Assay $2 \times 10^5$ HEK 293E cells were seeded in 12 well dishes 24 hours before transfection. Cells were transfected using Lipofectamine 2000 (Invitrogen) with 100 ng of pGL3 vectors (i.e. with Sirt-1 3'UTR wt or Sirt-1 3'UTR miR-181a del), 12 pmol of pre-miR-181a or pre-miR scramble sequence (Ambion), and 10 ng of *Renilla* luciferase pRL-CMV vector. Luciferase activities of cellular extracts were measured 24 hours after transfection, by using a Dual Luciferase Reporter Assay System (Promega); light emission was measured over 10 seconds using an OPTOCOMP I luminometer. Efficiency of transfection was normalised using *Renilla* luciferase activity.

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA). Anti-Sirt-1 (Abcam, Cambridge, United Kingdom; 1/500 dilution), anti-β actin (Sigma, St Louis, Minn., USA; 1/5000 dilution), were used.

Results miR-181a levels in senescing and differentiating keratinocytes

At p1 and p4, cells were collected to perform Real time PCR. Relative quantification of miR-181a levels between p1 and p4 shows significant increase in miR-181a expression in senescent keratinocytes: at p4, miR-181a expression is around 1.3 (±0.05) higher than its expression at p1 (which is equal to 1.00±0.03).

To the contrary, in proliferating keratinocytes, after 7 days of calcium treatment, miR-181a expression is around 0.93 (±0.029), whereas at day 0 it is 1.00 (±0.029).

Therefore, the keratinocyte senescent state, but not the keratinocyte proliferating state, is associated with an increase in miR-181a expression.

miR-181a targets Sirt-1 mRNA at 3'UTR

Bioinformatic analysis suggests that SirT1 is a putative target for miR-181a (FIG. 6A). The insertion of Sirt-1 3'UTR wt in a luciferase reporter gene leads to diminished luciferase activity in the presence of pre-miR-181a (0.648±0.1 fold over control). Additional control cells were transfected with pre-miR-217 (a known miR targeting Sirt-1 3'UTR) as positive control: the luciferase activity in this case is 0.35±0.0096 fold over control (FIG. 6B).

The insertion of Sit 3'UTR miR-181a del in a luciferase reporter gene leads to a slightly decreased luciferase activity in the presence of pre-miR-181a (0.93±0.09 fold over control). Additional control cells transfected with pre-miR-217 show a luciferase activity 0.3±0.07 fold over control (FIG. 6B). As shown in FIG. 6C, SirT1 protein is markedly diminished in human keratinocytes transfected with pre-miR-181a versus human keratinocytes transfected with a scrambled sequence (Ctrl). β-actin protein levels are reported as a loading control. These data demonstrate that SirT1 is a miR-181a target.

Modulation of miR-181a by Synthetic Compounds

Primary human keratinocytes were plated in EpiLife with HKGS growth supplements and treated with an anti-miR-181a at different concentrations. After 48 hours cells were harvested for relative quantification of miR-181a levels using Real time PCR. The anti-miR-181a is significantly down-regulating miR-181a levels with respect to the untreated cells; the expression of miR-181a in treated cells is only 0.075±0.052 (whereas it is 1.00±0.029 for scramble) (FIG. 7).

EXAMPLE 5

Expression of miR-191 During Keratinocyte Induced Senescence

Material and Methods

Cell Culture and Transfection

The human primary keratinocytes described in Example 1 are used in this example. Human primary keratinocytes were cultured in EpiLife medium with HKGS growth supplements (Cascade) and treated with CaCl2 1.2 mM in order to induce the differentiation process. Differentiated cells were harvested after 7 days of treatment for microRNA levels analysis. Human primary keratinocytes were transfected with human pre-miR-191, anti-miR-191 and Cy3-labeled negative control (Ambion, Texas, USA) using the SiPORT neoFX transfection agent (Ambion) according to manufacturer protocols. 16 hrs after transfection, the medium was removed and replaced with fresh medium.

800.000 human primary keratinocytes were plated in EpiLife with HKGS growth supplements and treated with test compounds. After 48 hours cells were harvested for microRNA levels analysis. HEK 293E cells were grown in D-MEM High glucose with 10% FBS, 100 U penicillin, 100 μg streptomycin (GIBCO, Invitrogen).

HEK 293E cells were transfected by Lipofectamine 2000 according to manufacturer protocols (Invitrogen). Hekn cells were treated with the test compounds for 48 hours. Cells were collected and mRNA extracted following standard procedures. Real time PCR were performed as described below.

RNA Extraction and Real Time PCR Analysis

Total RNA from cells or tissue was isolated using mirVana mirRNA Isolation Kit (Ambion) by following the manufacturer's protocol for total RNA extraction. Total RNA was quantified using a NanoDrop Spectophotometer (Thermo Scientific, Delaware, USA) and RNA quality was controlled on an agarose gel. For microRNA detection, RNA was reverse transcribed using TaqMan MicroRNA Reverse Transcription kit and qRT-PCR was performed with TaqMan universal master mix (Applied Biosystem) and specific primers for miR-191. U18 was used as an internal control (Applied Biosystem). The expression of each gene and miR was defined from the threshold cycle (Ct), and relative expression levels were calculated by using the 2-ΔΔCt method after normalization with reference to the expression of the housekeeping gene U18.

Senescence-Associated β-Galactosidase Staining

Cells were grown in 6-well culture plates, washed with PBS, and fixed with 2% formaldehyde/0.2% glutaraldehyde in PBS for 5 minutes. After another washing step with PBS, cells were incubated with β-galactosidase staining solution (150 mmol/L NaCl, 2 mmol/L MgCl2, 5 mmol/L potassium ferricyanide, 5 mmol/L potassium ferrocyanide, 40 mmol/L citric acid, 12 mmol/L sodium phosphate, pH 6.0, containing 1 mg/mL 5-bromo-4-chloro-3-indolyl-β-Dgalactoside [X-gal]) for 24 hours at 37° C. The reaction was stopped by replacing the staining solution with 70% glycerol.

Cell Proliferation and Cell Cycle Analysis

Methods used to evaluate cell proliferation are generally based on incorporation of thymidine analogues such as 3H thymidine or bromodeoxyuridine (BrdU) during DNA synthesis. The Click-iT™ EdU flow cytometry assay kit is a novel alternative to BrdU assay (Molecular Probes, Eugene, Oreg., USA). This method replaces antibody-based detection of the nucleoside analogue, BrdU, with EdU (5-ethynyl-2'-deoxyuridine), which is a nucleoside analogue of thymidine that is incorporated into DNA during active DNA synthesis. Briefly, cells were incubated with EdU for 4 hrs. After incubation, samples were fixed, permeabilized and stained according to the manufacturer's protocol. Cell cycle was analysed using a FACSCalibur flow cytometer (BD Biosciences, San Jose, Calif., USA). Fifteen thousand events were evaluated using the Cell Quest (BD) and Modfit LT (Verity Software; BD) programs.

Bioinformatics

Analysis of miR-191 target sites on CDK6 3'UTR were performed using the TargetScan 5.1 software available at http://www.targetscan.org/

Luciferase Assay $2 \times 10^5$ HEK 293E cells were seeded in 12 well dishes 24 hours before transfection. Cells were transfected using Lipofectamine 2000 (Invitrogen) with 100 ng of pGL3 vectors 12 pmol of pre-miR-191 or pre-miR scramble sequence (Ambion), and 10 ng of *Renilla* luciferase pRL-CMV vector. Luciferase activities of cellular extracts were measured 24 hours after transfection, by using a Dual Luciferase Reporter Assay System (Promega); light emission was measured over 10 seconds using an OPTOCOMP I luminometer. Efficiency of transfection was normalised using *Renilla* luciferase activity.

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA).

Polyclonal anti-CDK-6 (Santa Cruz, sc-177, dilution 1:2000), anti-β actin (Sigma, St Louis, Minn., USA; 1/5000 dilution), were used.

Results miR-191 Levels in Senescing and Differentiating Keratinocytes

At p1 and p4, cells were collected to perform Real time PCR. Relative quantification of miR-191 levels between p1 and p4 shows significant increase in miR-191 expression in senescent keratinocytes: at p4, miR-191 expression is around 1.9 (±0.07) higher than its expression at p1 (which is equal to 1.0±0.04). To the contrary, in proliferating keratinocytes, after 7 days of calcium treatment, miR-191 expression is around 0.41 (±0.019), whereas at day 0 it is 1.0 (±0.02).

Therefore, the keratinocyte senescent state, but not the keratinocyte proliferating state, is associated with an increase in miR-191 expression.

miR-191 Targets CDK6 mRNA at 3'UTR

Bioinformatic analysis suggests that CDK6 is a putative target for miR-191 (FIG. 8A). The insertion of CDK6 3'UTR wt in a luciferase reporter gene leads to diminished luciferase activity in the presence of pre-miR-191 (0.78±0.1 fold over control), (FIG. 6B). As shown in FIG. 8C, CDK6 protein is markedly diminished in human keratinocytes transfected with pre-miR-1)1 versus human keratinocytes transfected with a scrambled sequence (Ctrl). β-actin protein levels are reported as a loading control. These data demonstrate that CDK6 is a miR-191 target.

Modulation of miR-191 by Synthetic Compounds

Primary human keratinocytes were plated in EpiLife with HKGS growth supplements and treated within anti-miR-191 at different concentrations. After 48 hours cells were harvested for relative quantification of miR-191 levels using Real time PCR. The anti-miR-191 is significantly downregulating miR-191 levels with respect to the untreated cells; the expression of miR-191 in treated cells is only 0.061±0.049 (whereas it is 1.00±0.019 for scramble) (FIG. 9).

EXAMPLE 6

Over-Expressions of miR-130a, miR-138, miR-181a and miR-191 in Proliferating Keratinocytes Material and Methods Cell Culture and Transfection The human primary keratinocytes described in Example 1 are used in this example. Human primary keratinocytes were cultured in EpiLife medium with HKGS growth supplements (Cascade). Human primary keratinocytes were transfected with human pre-miR-130a, -138, -181a, -191 and Cy3-labeled negative control (Ambion, Texas, USA) using the SiPORT neoFX transfection agent (Ambion) according to manufacturer protocols. 16 hrs after transfection, the medium was removed and replaced with fresh medium.

Senescence-Associated β-Galactosidase Staining

Cells were plated in 6-well culture plates, washed with PBS, and fixed with 2% formaldehyde/0.2% glutaraldehyde in PBS for 5 minutes. After another washing step with PBS, cells were incubated with β-galactosidase staining solution (150 mmol/L NaCl, 2 mmol/L MgCl2, 5 mmol/L potassium ferricyanide, 5 mmol/L potassium ferrocyanide, 40 mmol/L citric acid, 12 mmol/L sodium phosphate, pH 6.0, containing 1 mg/mL 5-bromo-4-chloro-3-indolyl-β-Dgalactoside [X-gal]) for 24 hours at 37° C. The reaction was stopped by replacing the staining solution with 70% glycerol.

Cell Proliferation and Cell Cycle Analysis

Methods used to evaluate cell proliferation are generally based on incorporation of bromodeoxyuridine (BrdU) during DNA synthesis. The Click-iT™ EdU flow cytometry assay kit is a novel alternative to BrdU assay (Molecular Probes, Eugene, Oreg., USA). This method replaces antibody-based detection of the nucleoside analogue, BrdU, with EdU (5-ethynyl-2'-deoxyuridine), which is a nucleoside analogue of thymidine that is incorporated into DNA during active DNA synthesis. Briefly, cells were incubated with EdU for 4 hrs. After incubation, samples were fixed, permeabilized and stained according to the manufacturer's protocol. Cell cycle was analysed using a FACSCalibur flow cytometer (BD Biosciences, San Jose, Calif., USA). Fifteen thousand events were evaluated using the Cell Quest (BD) and Modfit LT (Verity Software; BD) programs.

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA).

Anti-p63 (Ab4, Neomarkers, Fremont, Calif., USA; 1/500 dilution), anti-β actin (Sigma, St Louis, Minn., USA; 1/5000 dilution), anti-p16 (Santa Cruz Biotechnology, California, USA; dilution 1:1000) were used.

Results

Over-Expression of miR130a in Keratinocytes is not a Significant Effect on Proliferation and Induction of Cellular Senescence In Vitro Conditions Upon miR-130a overexpression no effects were detected on proliferation and senescence, as evaluated by BrdU incorporation and SA-β-galactosidase staining (FIG. 10). These results are due to the fact that miR-130a, in this specific in vitro conditions, is not able to inhibit completely p63 expression. Being p63 still expressed in the cells upon miR-130a transfection (see FIG. 11C), we can not detect the effects on proliferation and senescence. However, miR-130a is up-regulated in vivo in the keratinocytes of old subjects (see below, FIG. 14) and in replicative-induced senescence (see Example 2), demonstrating its involvement in cellular senescence.

Over-Expression of miR-138 in Keratinocytes is Sufficient to Inhibit Proliferation and Induce Cellular Senescence Upon miR-138 overexpression in proliferating keratinocytes, we detected a strong effect on inhibition of proliferation as evaluated by BrdU incorporation and SA-β-galactosidase staining (FIG. 11), indicating that miR-138 is sufficient per se to induce senescence. Statistical evaluation shows a significantly variation upon miR-138 transfection (±s.d. *p-value<0.01, **p-value<0.005 by Student t test) (FIG. 11) in both proliferation and induction of senescence.

Over-Expression of miR-181a in Keratinocytes is Sufficient to Inhibit Proliferation and Induce Cellular Senescence Upon miR-181a overexpression in proliferating keratinocytes, we detected a strong effect on inhibition of proliferation as evaluated by BrdU incorporation and SA-β-galactosidase staining (FIG. 12), indicating that miR-181a is sufficient per se to induce senescence. Statistical evaluation shows a significantly variation upon miR-181a transfection (±s.d. *p-value<0.01, **p-value<0.005 by Student t test) (FIG. 11) in both proliferation and induction of senescence.

Over-Expression of miR-191 in Keratinocytes is Sufficient to Inhibit Proliferation and Induce Cellular Senescence Upon miR-191 overexpression we detected a strong effect on inhibition of proliferation as evaluated by BrdU incorporation and SA-β-galactosidase staining (FIG. 13), indicating that miR-191 is sufficient per se to induce senescence. Statistical evaluation shows a significantly variation upon miR-191 transfection (±s.d. *p-value<0.01, **p-value<0.005 by Student t test) (FIG. 13) in both proliferation and induction of senescence.

EXAMPLE 7

Expression of miR-130a, miR-138, miR181a and miR-191 in Keratinocytes Obtained by Young and Old Subjects Material and Methods Cell and Culture Conditions, Western Blotting and miRs Analysis from Skin Biopsies Protein extracts from human skin keratinocytes of young and old individuals were obtained by the Dermatology Department (IDI-IRCCS), following the procedure described in Cordisco et al JID 130:1048-1062 (2010). Relative quantifications of miR-130a, miR-138, miR-181a and miR-191 were performed as already described in Examples 2 to 5 respectively.

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA).

Anti-p63 (Ab4, Neomarkers, Fremont, Calif., USA; 1/500 dilution), anti-β actin (Sigma, St Louis, Minn., USA; 1/5000 dilution), anti-p16 (Santa Cruz Biotechnology, California, USA; dilution 1:1000), anti-Sirt-1 (Abcam, Cambridge, United Kingdom; 1/500 dilution), were used.

Results

To validate our finding in humans subjects, we have studied the expression of p63 and SirT1 in keratinocytes isolated by young (7 and 10 years old) and old (70 and 76 years old) subjects. Western blot analysis indicate that both p63 and SirT1 expression levels are high in keratinocytes from young subjects in comparison to the old one (FIG. 14A). This was similar to the in vitro replicative-induced senescence (FIG. 14B). By real time PCR, we evaluated the expression level of the miRs in the cells of the selected subjects (FIG. 14C-F). MiR-130a, miR-138, miR-181a and miR-191 are up-regulated also in vivo in the keratinocytes of old subjects (see FIG. 14) in comparison to young ones, demonstrating that these microRNAs are involved in senescence also in vivo aged skin.

EXAMPLE 8

Active Compounds

Material and Methods
Cell Culture

Neonatal Human Primary Epidermal Keratinocytes (Hekn, Cascade, Invitrogen, Carlsbad, Calif., USA) were cultured in EpiLife medium added with HKGS growth supplements (Cascade). Cells were constantly kept subconfluent in order to avoid triggering of a differentiation process. Cells were passaged usually once a week, at each passage the harvested cells number and seeded cell number were recorded in order to calculate the population doublings occurring between passages and the population doubling time. At passage 2 300.000 keratinocytes were plated in 60 mm dishes. The day after the cells were treated with the compounds at the indicated concentration for 48 hours without changing of the media. Cells were collected by scraping in medium. Cells were centrifuged at 800 g for 5 min and RNA was extracted.

RNA Extraction and Real Time PCR Analysis

Total RNA from cells was isolated using mirVana mirRNA Isolation Kit (Ambion) by following the manufacturer's protocol for total RNA extraction. Total RNA was quantified using a NanoDrop Spectophotometer (Thermo Scientific, Delaware, USA) and RNA quality was controlled on an agarose gel. For microRNA detection, RNA was reverse transcribed using TaqMan MicroRNA Reverse Transcription kit and qRT-PCR was performed with TaqMan universal master mix (Applied Biosystem) and specific primers for miR-130a, -138, -181a and -191. U18 was used as an internal control (Applied Biosystem). The expression of each gene and miR was defined from the threshold cycle (Ct), and relative expression levels were calculated by using the 2-$\Delta\Delta$Ct method after normalization with reference to the expression of the housekeeping gene U18.

The following compounds were tested according to the process of the invention, and the following results were obtained:

|  | Mir 130a | Mir 138 | Mir 181a | Mir 191 |
|---|---|---|---|---|
| Gingerol 6 | >20 (37%) (6. 10-5%) |  | >20 (29%) (6. 10-5%) | >20 (24%) (6. 10-5%) |
| Reversage |  | >20 (22%) (2,5. 10-6%) |  |  |
| Tryacetyl-leukodopachrome methyl ester | 20 (10-3%) |  |  |  |
| Resveratrol | >20 (25%) (4. 10-4%) |  | >20 (21%) (4. 10-4%) |  |

EXAMPLE 9

Cosmetic Composition (O/W Serum)

The following composition may be prepared in a classical manner for the man skilled in the art.

| INCI name | % (w/w) |
|---|---|
| Water | QSP 100.00 |
| Chelating agent | 0.05 |
| pH balance | 0.05 |
| Preservatives | 0.05 |
| Glycol | 3.25 |
| AMMONIUM ACRYLOYLDIMETHYLTAURATE/ VP COPOLYMER | 1.20 |
| ACRYLATES/C10-30 ALKYL ACRYLATE CROSSPOLYMER | 0.20 |
| GLYCERIN | 3.00 |
| GLYCERYLPOLYMETHACRYLATE | 4.18 |
| SODIUM ACETYLATED HYALURONATE | 0.05 |
| Oil | 10.00 |
| ALCOHOL | 8.00 |
| PERFUMES | 0.30 |
| Resveratrol | 0.05 |

REFERENCES

Serrano et al (1997), Cell 88:593-562
Campisi (2001), Trends Cell Biol 11:S27-S31
Schmitt et al (2002) Cell 109:335-346
Narita et al (2003), Cell 113:703-706
Sharpless et al 2004) J Clin Invest 113:160-168
Campisi (2005) Cell 120:513-522
Yang et al (1999), Nature 398: 714-718
Mills et al (1999), Nature 398: 708-713
Lena et al (2008), Cell Death Differ 15:1187
Yi et al (2008), Nature 452:225
Bernstein et al (2003), Nature Genetics 35:215-217
Keyers et al (2005), Genes and Dev 19:1986-1999
Mudhasani et al (2008), J Cell Biol 181:1055-1063
Sommer et al (2006), Cell Cycle 5:2005-2011
Kohrt D M et al (2009), Cell Cycle 8:2837-43
Grossel M J et al (2006) J Cell Biochem 97(3):485-93.

---

The invention claimed is:

1. An in vitro method for screening for candidate compounds for attenuating ageing of the skin, and/or for hydrating the skin, comprising the following steps:
  a. bringing at least one test compound in contact with a sample of isolated pre-senescent neonatal human primary epidermal keratinocytes cultured in vitro, wherein the keratinocytes are obtained after culturing in Medium 154 with added Human Keratinocyte Growth Supplement (HKGS) and continually keeping the keratinocytes in a subconfluent state for at least 37 population doublings;
  b. measuring the expression level of at least one microRNA in said keratinocytes, wherein the expression level of said at least one microRNA is measured by qRT-PCR or real-time PCR;
  c. comparing the expression level of said at least one microRNA measured in step b to the expression level of said at least one microRNA in untreated keratinocytes which have not been in contact with said at least one test compound; and
  d. selecting a test compound in which the expression of said at least one microRNA is inhibited by at least 20% compared with said untreated keratinocytes, wherein the at least one microRNA is selected from the group consisting of miR-138, miR-181a and miR-191.

2. The method according to claim 1, wherein step b is performed before and after step a.

3. The method according to claim 1, comprising the following steps:
  a'. preparing at least two samples of said isolated keratinocytes cultured in vitro;
  a. bringing at least one of the at least two samples into contact with the at least one test compound, while leaving at least one of the at least two samples untreated and not in contact with the at least one test compound; then
  b. measuring the expression level of the at least one microRNA in said treated and untreated samples;
  c. comparing the expression level of said at least one microRNA measured in the treated sample to the expression level of said at least one microRNA in the untreated sample; and
  d. selecting a test compound in which the expression of said at least one microRNA in the treated sample is inhibited by at least 20% compared with the untreated sample.

4. The method according to claim 1, wherein the test compounds are botanical extracts.

5. The method according to claim 1, wherein the expression of said at least one microRNA is inhibited by at least 50% compared with said untreated keratinocytes.

6. The method according to claim 1, wherein the expression of said at least one microRNA is inhibited by at least 60% compared with said untreated keratinocytes.

* * * * *